US005874088A

United States Patent [19]

[11] Patent Number: 5,874,088
[45] Date of Patent: Feb. 23, 1999

Mekalanos

[54] DELETION MUTANTS OF CHOLERA VACCINES EXPRESSING HETEROLOGOUS ANTIGENS

[75] Inventor: John J. Mekalanos, Cambridge, Mass.

[73] Assignee: President and Fellows of Harvard College, Cambridge, Mass.

[21] Appl. No.: 367,115

[22] PCT Filed: Jul. 1, 1993

[86] PCT No.: PCT/US93/06270

§ 371 Date: Jun. 28, 1995

§ 102(e) Date: Jun. 28, 1995

[87] PCT Pub. No.: WO94/01533

PCT Pub. Date: Jan. 20, 1994

Related U.S. Application Data

[63] Continuation-in-part of Ser. No. 83,388, Jun. 28, 1993, abandoned, which is a continuation of Ser. No. 909,382, Jul. 6, 1992, abandoned.

[51] Int. Cl.[6] ............................ A61K 39/106; C12N 1/21

[52] U.S. Cl. .................................... 424/200.1; 424/261.1; 424/235.1; 424/203.1; 435/252.1; 435/252.3; 435/243; 435/69.3; 435/909

[58] Field of Search ............................. 424/200.1, 261.1, 424/235.1, 243, 203.1; 435/69.3, 252.3, 243, 252.1, 909

[56] References Cited

U.S. PATENT DOCUMENTS 4,882,278 11/1989 Mekalanos .
4,935,364 6/1990 Kaper et al. .
5,098,998 3/1992 Mekalanos et al. .

FOREIGN PATENT DOCUMENTS

WO 91/18979 12/1991 WIPO .

OTHER PUBLICATIONS

Pinkerton et al. Science 262:160–162, Oct. 1993.

Gregory D. Pearson et al. CTX Genetic Element Encodes a Site–Specific Recombination System and an Intestinal Colonization Factor, Proc. Natl. Acad. Sci. USA, vol. 90, 3750–3754, 1993.

Kathleen Richardson et al. "Transposon–Induced non–motile mutants of Vibrio Cholerae" Journal of General Microbiology, vol. 136, 717–725, 1990.

Cash et al., "Response of Man to Infection with *Vibrio cholerae*, II, Protection from Illness Afforded by Previous Disease and Vaccine", Journal of Infectious Diseases 130:325–333, 1974.

Finkelstein, "Cholera", Critical Reviews in Microbiology 2:553–623, 1973.

Freter et al., "Adhesive Properties of *Vibrio cholerae*: Nature of the Interaction With Intact Mucosal Surfaces" Infection and Immunity 14:246–256, 1976.

Freter et al., "Role of Chemotaxis in the Association of Motile Bacteria With Intestinal Mucosa: Fitness and Virulence of Nonchemotactic *Vibrio cholerae* Mutants in Infant Mice" Infection and Immunity 34:222–233, 1981.

Freter et al., "Role of Chemotaxis in the Association of Motile Bacteria with Intestinal Mucosa: In Vivo Studies" Infection and Immunity 34:234–240, 1981.

Guentzel et al., "Motility as a Virulence Factor for *Vibrio cholerae*" Infection and Immunity 11:890–897, 1975.

Herrington et al., "Toxin, Toxin–coregulated Pili, and the toxR Regulon are Essential for *Vibrio Cholerae* Pathogenesis in Humans", J. Experimental Medicine 168:1487–1492, 1988.

Jones et al., "Adhesive Properties of *Vibrio cholerae*: Adhesion to Isolated Rabbit Brush Border Membranes and Hemagglutinating Activity" Infection and Immunity 14:232–239, 1976.

Jones et al., "Adhesive Properties of *Vibrio cholerae*: Nature of the Interaction With Isolated Rabbit Brush Border Membranes and Human Erythrocytes", Infection and Immunity 14:240–245, 1976.

Kaper et al., "A Recombinant Live Oral Cholera Vaccine", Biotechnology, Apr. 1984, pp. 345–349.

Kaper et al., "Recombinant nontoxinogenic *Vibrio cholerae* strains as attenuated cholera vaccine candidates" Nature 308:655–658, 1984.

Levine et al., "Duration of Infection–Derived Immunity to Cholera", J. Infectious Diseases 143:818–820, 1981.

Levine et al., "The Pathogenicity of Nonenterotoxigenic *Vibrio cholerae* Serogroup 01 Biotype El Tor Isolated from Sewage Water in Brazil", J. Infectious Diseases 145:296–299, 1982.

Levine et al., "Volunteer Studies of Deletion Mutants of *Vibrio cholerae* 01 Prepared by Recombinant Techniques" Infection and Immunity 56:161–167, 1988.

Levine et al., "Safety, immunogenicity, and efficacy of recombinant live oral cholera vaccines, CVD 102 and CVD 103–HgR", The Lancet II:467–470, 1988.

Mekalanos, "Duplication and Amplification of Toxin Genes in *Vibrio cholerae*", Cell 35:253–263, 1983.

Mekalanos et al., "Cholera toxin genes: nucleotide sequence, deletion analysis and vaccine development", Nature 306:551–557, 1983.

Mekalanos et al., "Isolation of enterotoxin structural gene deletion mutations in *Vibrio cholerae* induced by two mutagenic vibriophages" PNAS USA 79:151–155, 1982.

(List continued on next page.)

*Primary Examiner*—Anthony C. Caputa
*Attorney, Agent, or Firm*—Clark & Elbing LLP; K. Bieker-Brady

[57] ABSTRACT

The invention features a nontoxigenic genetically stable mutant strain of *V. cholerae* which lacks any functional attRS1 sequences is useful as a live, oral vaccine for inducing immunological protection against cholera and a method for making same. The invention also features a killed, oral cholera vaccine comprising at least a first and a second *V. cholerae* strain, wherein at least one of the strains is a different serotype, and the vaccine also contains cholera toxin B subunit, produced by at least one of the serotypes.

44 Claims, 6 Drawing Sheets

OTHER PUBLICATIONS

Mostow et al., "High–Frequency Spontaneous Mutation of Classical *Vibrio cholerae* to a Nonmotile Phenotype", Infection and Immunity 58:3633–3639, 1990.

Pearson et al., "New Attenuated Derivatives of *Vibrio cholerae*", Res. Microbiol. 141:893–899, 1990.

Pierce et al., "Determinants of the Immunogenicity of Live Virulen and Mutant *Vibrio cholerae* 01 in Rabbit Intestine", Infection and Immunity 55:477–481, 1987.

Richardson, "Roles of motility and flagellar structure in pathogenicity of *Vibrio cholerae*: Analysis of motility mutants in three animal models", Infection and Immunity 59:2727–2736, 1991.

Richardson et al., Transposon–induced non–motile mutants of *Vibrio cholerae*, J. General Microbiology 136:717–725, 1990.

Taylor et al., "Use of phoA gene fusions to identify a pilus colonization factor coordinately regulated with cholera toxin", PNAS USA 84:2833–2937, 1987.

Taylor et al., "Safe, live *Vibrio cholerae* vaccines?" Vaccine 6:151–154, 1988.

Teppema et al., "In vivo Adherence and Colonization of *Vibrio cholerae* Strains That Differ in Hemagglutinating Activity and Motility", Infection and Immunity 55:2093–2102, 1987.

van de Walle et al., "Production of cholera toxin subunit B by a mutant strain of *Vibrio cholerae*", Applied Microbiology Biotechnology 33:389–394, 1990.

Wachsmuth et al., "Difference between toxigenic *Vibrio cholerae* 01 from South America and US gulf coast", The Lancet 337:1097–1098, 1991.

Yamamoto et al., "*Vibrio cholerae* 01 Adherence to Villi and Lymphoid Follicle Epithelium: In Vitro Model Using Formalin–Treated Human Small Intestine & Correlation between Adherence & Cell–Associated Hemagglutinin Levels", Infection and Immunity 56:3241–3250, 1988.

Yancey et al.,"Role of Motility in Experimental Cholera in Adult Rabbits", Infection and Immunity 22:387–392, 1978.

Bhattacharjee et al., "Adherence of Wild–type and Mutant Strains of *Vibrio cholerae* to Normal and Immune Intestinal Tissue," Bulletin of the World Health Organization 57(1):123–128, 1979.

Blair et al., "Mutant MotB Proteins in *Escherichia coli*," Journal of Bacteriology 173:4049–4055, 1991.

Chun et al., "Bacterial Motility: Membrane Topology of the *Escherichia coli* MotB Protein," Science 239:276–277, 1988.

Hughes et al., "Sequence analysis of the *Vibrio cholerae* acfD gene reveals the presence of an overlapping reading frame . . . Salmonella," Gene 146:79–82, 1994.

McCarter et al., "Identification of Genes Encoding Components of the Swarmer Cell Flagellar Motor and Propeller and a Sigma Factor . . . parahaemolyticus," Journal of Bacteriology 175:3361–3371, 1993.

Wei et al., "Covalent Structure of Three Phase–1 Flagellar Filament Proteins of Salmonella," Journal of Molecular Biology 186:791–803, 1985.

DELETION MUTANTS OF CHOLERA VACCINES EXPRESSING HETEROLOGOUS ANTIGENS

This application is a continuation-in-part of U.S. Ser. No. 08/083,388, Jun. 28, 1993, now abandoned which is a continuation of U.S. Ser. No. 07/909,382, filed Jul. 6, 1992, now abandoned.

BACKGROUND OF THE INVENTION

The field of invention is *Vibrio cholerae* vaccines. After more than 100 years of research on cholera, there remains a need for an effective cholera vaccine. There have been six pandemics of this disease caused by strains of *V. cholera* belonging to the "Classical" biotype. The etiological agents of the current (seventh) pandemic belong to the "El Tor" biotype (Finkelstein, Crit. Rev. Microbiol 2:553–623, 1973, Wachsmuth et al., The Lancet 337:1097–1098, 1991). Recently the seventh pandemic has extended to a new locale, that of South America. Beginning in January of 1991, an epidemic of cholera resulted in greater than 250,000 cases and over 2,000 deaths in Peru, Ecuador, Columbia, and Chile. Before this epidemic it was estimated that over 200,000 cases of cholera occurred per year mainly in India, Bangladesh, Africa and Western Asia (Tacket et al., Cholera Vaccines. In *Vaccines: New Approaches to Immunological Problems*, Ellis, R. W., editor, Butterworth-Heinemann, Boston, 1992).

In November of 1992, an antigenically distinct, non-01 form of *V. cholerae* emerged in India and Bangladesh and within eight months caused an estimated 500,000 cases and 6,000 deaths. The pandemic potential of this new strain, designated serogroup 0139 synonym "Bengal", seems assured and is a new cause of concern throughout the developing world. These recent experiences underline the need for effective cholera vaccines against disease due to both El Tor 01 and Bengal 0139 serotypes of *V. cholerae*.

Because natural infection by and recovery from cholera induces immunity lasting at least 3 years (Tacket et al., Supra; Levine et al., J. Infect. Dis. 143:818–820, 1981; Cash et al., J. Infect. Dis. 130:325–333, 1974), much effort has been made to produce live, attenuated cholera vaccines that when administered orally would mimic the disease in its immunization properties but would not cause adverse symptoms or reactions in the immunized individual (i.e., display low reactogenicity). Vaccines of this type involve deletion mutations that inactivate the gene encoding the A subunit of cholera toxin, a protein which is responsible for most of the diarrhea seen in this disease (Mekalanos et al., Proc. Natl. Acad. Sci. U.S.A. 79:151–155, 1982; Mekalanos et al., Nature 306:551–557, 1983; Kaper et al., Nature 308:655–658, 1984; Kaper et al., Biotechnology 2:345, 1984; Pierce et al., Infect. Immun. 55:477–481, 1987; Taylor et al., Vaccine 6:151–154, 1988; Levine et al., Infn. Immun. 56:161–167, 1988; Herrington et al. J. Exper. Med. 168:1487–1492, 1988; Levine et al., Lancet ii:467–470, 1988; Kaper et al., Res. Microbiol. 141:901–906, 1990; Pearson et al., Res. Microbiol. 141:893–899, 1990). See also Mekalanos, U.S. Pat. Nos. 5,098,998 and 4,882,278, and Kaper et al., U.S. Pat. No. 4,935,364, hereby incorporated by reference. While both oral, killed whole cell vaccines and several live, attenuated cholera vaccine have been developed, the most promising of these provide little protection against the El Tor biotype of *V. cholerae* and probably no protection against the 0139 serotype. The major issues associated with cholera vaccines are safety, stability and their degree of antigenicity.

With regard to the toxin genes of *V. cholerae*, the genetic diversity among toxigenic and non-toxigenic strains has been examined by Chen et al. (1991, Epidemiol. Infect. 107:225). Mekalanos (1983, Cell 35:253) reports on the duplication and amplification of *V. cholerae* toxin genes, and Miller et al. (1984, Proc. Natl. Acad. Sci. U.S.A. 81:3471) discusses transcriptional regulation of the toxin genes. Other *V. cholerae* genes whose products may play a role in the pathogenicity of this organism include the toxin-coregulated pilus genes (Shaw et al., 1990, Infect. Immun. 58:3042; Sharma et al., 1989, Vaccine, 7:451; Sun et al., 1990, J. Infect. Dis. 161:1231; Hall et al., 1991, Infect. Immun. 59:2508; Taylor et al., 1987, Proc. Natl. Acad. Sci. U.S.A. 84:2833), and the gene encoding the intestinal colonization factor (Taylor et al., 1988, Vaccine 6:151).

SUMMARY OF THE INVENTION

The invention features a nontoxigenic genetically stable mutant strains of *V. cholerae* which are useful as a live, oral vaccines for inducing immunological protection against cholera. The mutant strains are genetically engineered mutants which lack DNA encoding a functional ctxA subunit and also lack any functional attRS1 sequences. By attRS1 sequences is meant a 17 base pair sequence contained within the CTX genetic element that is required for recombination and amplification of the CTX genetic element, or enough of that sequence to enable such recombination and amplification. Mutants which "lack any functional attRS1 sequences" are those which substantially cannot undergo effective site-specific recombination with attRS1-containing vehicles, because the wild type attRS1 sequences are wholly deleted or are sufficiently deleted or mutated to prevent such recombination. As a result, *V. cholerae* strains according to the invention are safer because they cannot recombine with wild type attRS1-containing vehicles which include the ctxA-encoding DNA.

The invention also features a method of making the above described *V. cholerae* strains. The method involves introducing a plasmid into a wild type *V. cholerae* which contains a fragment of *V. cholerae* DNA containing a mutation in the ctxA and attRS1 sequences. The *V. cholerae* DNA fragment is capable of recombining with wild type *V. cholerae* DNA inside the organism to generate the mutant strain.

Although any serotype of *V. cholerae* may be used, in preferred embodiments, the mutant strain of *V. cholerae* belongs to the El Tor serotype, and more preferably, the Inaba or Ogawa serotype or the *V. cholerae* non-01 serotype, preferably 0139 "Bengal" serotype. Preferably, the mutants lack all of the CTX core and attRS1 sequences and more preferably the mutant strain is Peru-2, Bang-2, Bah-2, or an attenuated derivative of the Bengal serotype, such as Bengal-2 ("Beng-2") or Bengal-3 ("Beng-3") as described below.

Mutant strains according to the invention optionally include additional mutations introduced to improve the safety and/or the immunogenicity of the vaccine. Such additional mutations include, but are not limited to, inactivation of one or more genes involved in DNA recombination, for example the recA gene encoded by the strain, and the introduction of additional genes which may be introduced into the *V. cholerae* chromosome, preferably into the *V. cholerae* lacZ gene. Preferred additional genes include a gene encoding the B subunit of *V. cholerae* or any heterologous antigen such as the B subunit of Shiga-like toxin, or a gene encoding the *E. coli* CFA antigen, or an antigenic HIV antigen. By heterologous antigen is meant any antigen that is not normally expressed by *V. cholerae*. For example, the heterologous antigen may be Shigella lipopolysaccharide (LPS) antigen, Shiga-toxin, various CFA antigens of enterotoxigenic *E. coli* strains, anthrax toxin, Pseudomonas endotoxin A, antigenic fragments from the HIV capsid, pertussis toxin, tetnus toxin; antigens from Herpes virus, rubella virus, influenza virus, mumps virus, measles virus, poliomyelitis virus; and immunogenic polypeptides from eukaryotic parasites causing malaria, pneumocystis pneumonia, and toxoplasmosis, may be expressed in a *V. cholerae* live vaccine. Preferably, the mutant strain having additional mutations is Peru-14, Peru-3, Peru-4, Peru-5, Bang-3, Bang-5, Bah-3, Bah-4, Bah-5 or an attenuated derivative of Bengal.

By a ctxA subunit is meant the A subunit of the cholera toxin which is responsible, when functional, for many of the symptoms of cholera (e.g., nausea, diarrhea etc.). Most preferably, the strains include deletion of the entire so-called "core genetic element", includes not only the ctxA/B, but also a region known as ICF (Intestinal Colonization Factor, probably equivalent CEP "core encoded pilin") and ZOT, described in greater detail below.

In another aspect, the invention features a nontoxigenic genetically stable mutant strain of *V. cholerae* which is useful as a live, oral vaccine for inducing immunological protection against cholera. The mutant strain is a genetically engineered mutant which lacks DNA encoding a functional ctxA subunit. The strain may also be soft agar penetration-defective. By soft agar penetration-defective is meant lacking the ability to penetrate a media of high viscosity as measured in vitro by swarming on and within agar media which is between 0.25 and 0.4% agar. The preferable strain may also be fillamentous, i.e. 25% or more cells greater than 15 nM in length under conditions of logarithmic growth. In preferred embodiments the strain is also ATT−.

In preferred embodiments, the invention includes a vaccine comprising at least two different strains of *V. cholerae* which are nontoxigenic genetically stable mutants which lack DNA encoding a functional ctxA subunit and are also soft agar penetration-defective. One of the two strains is preferably derived from the Peru strain and the other one is derived from the Bengal strain. The invention also includes a vaccine in which each of thecomponent strains are $ctx^-$, $att^-$, and $recA^-$. Depending upon the relevant local epidemiology, the vaccine strains may be administered together in a single dose, or more preferably, separately 7–28 days apart. Where only one of the serotypes presents a threat of disease, it may be preferable to administer a vaccine regime comprising only one strain.

The invention also features a killed, oral cholera vaccine comprising at least a first and a second *V. cholerae* strain, wherein at least two of the strains are different serotypes and all strains in the mixture lack DNA encoding a functional ctxA subunit. The vaccine also contains cholera toxin B subunit produced by at least one of the serotypes. Preferably, one of the serotypes in the vaccine is an Ogawa serotype and another of the serotypes is an Inaba serotype. Most preferably, the killed oral vaccine comprises Bah-3 and either Peru-3 or Bang-3, or both Peru-3 and Bang-3, as defined below. Any of the oral vaccine combinations may also include cells of the Bengal serotype, as defined below, including Bengal-2 and Bengal-3. The strains may be administered singly, together, or in consecutive doses 7–28 days apart.

The invention also features a method of making a killed *V. cholerae* vaccine. The method involves growing at least a first and a second *V. cholerae* strain, wherein each strain in the mixture lacks DNA encoding a functional ctxA subunit. The strains are then collected from the growth medium and the cells are killed. Cholera toxin B subunit, produced by at least one of the strains is obtained from the medium in which the strain was propagated and is added to the killed cells. The mixture of killed bacteria and cholera toxin B subunit is then suspended in a physiologically acceptable carrier.

Mutants such as those described above are useful as cholera vaccines and are improved in their genetic properties compared with previous vaccines.

Other features and advantages of the invention will be apparent from the following description of preferred embodiments thereof, and from the claims.

DETAILED DESCRIPTION

The drawings will first be briefly described.

The Drawings

Figure 1:
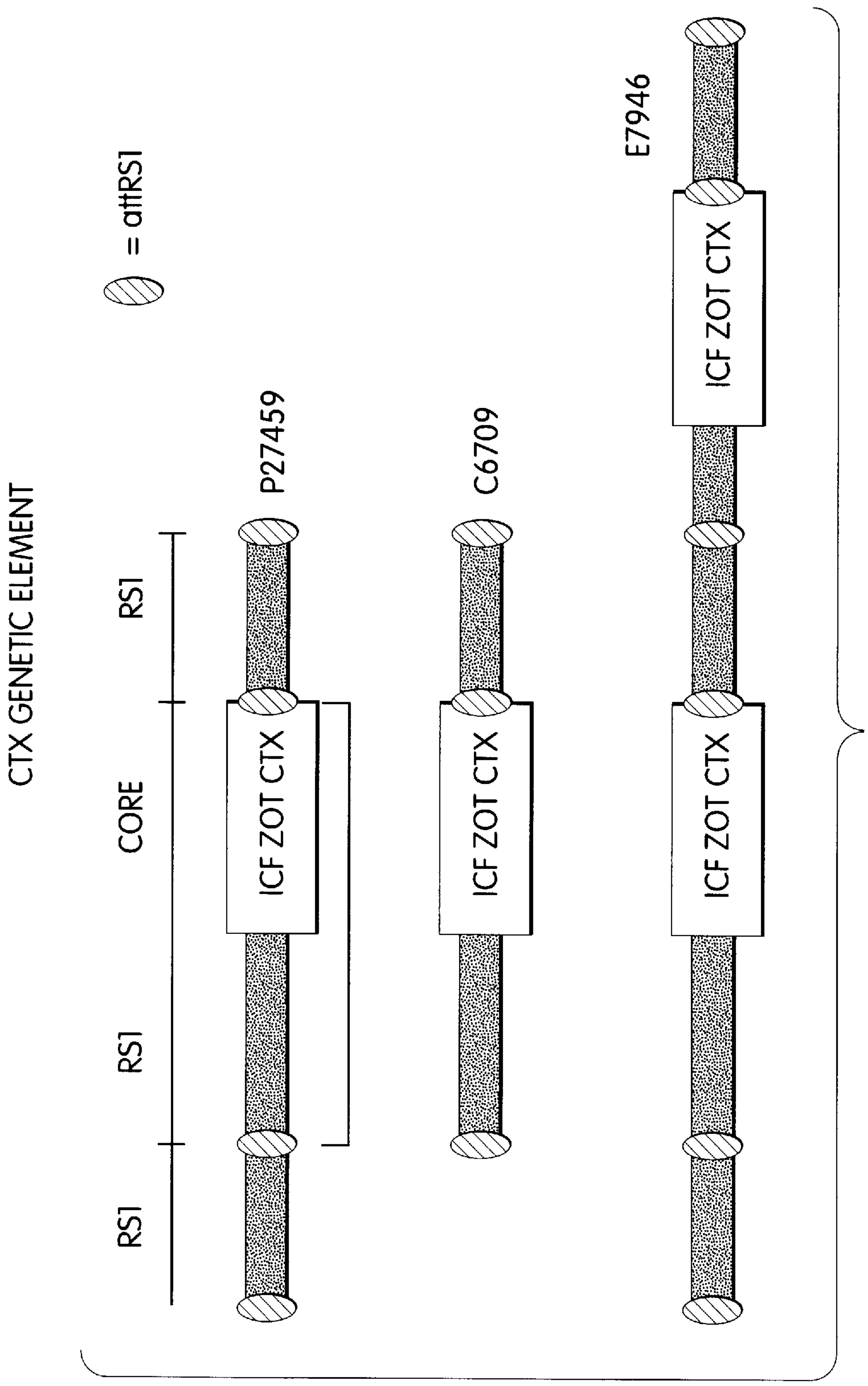

FIG. 1. is a schematic diagram of the CTX genetic elements of toxigenic *V. cholerae* strains P27459-Sm, C6709-Sm and E7946-Sm. The filled in boxes represent RS1 sequences. Between the RS1 sequences is a region shown as an open box (called the core region) which contains the ctxAB genes and genes encoding zot, the intestinal colonization factor (ICF). At the ends of the RS1 sequences are filled in circles that represent copies of sequences that match 16 out of 17 bases with the 17 base pair sequence attRS1 (CCTAGTGCGCATTATGT) [SEQ.ID.NO:1]. Although the CTX elements of the three strains vary in their structure based on the number of copies of the RS1 and core regions, it should be noted that these elements are inserted into the same chromosomal site in all El Tor strains of *V. cholerae.*

Figure 2A:
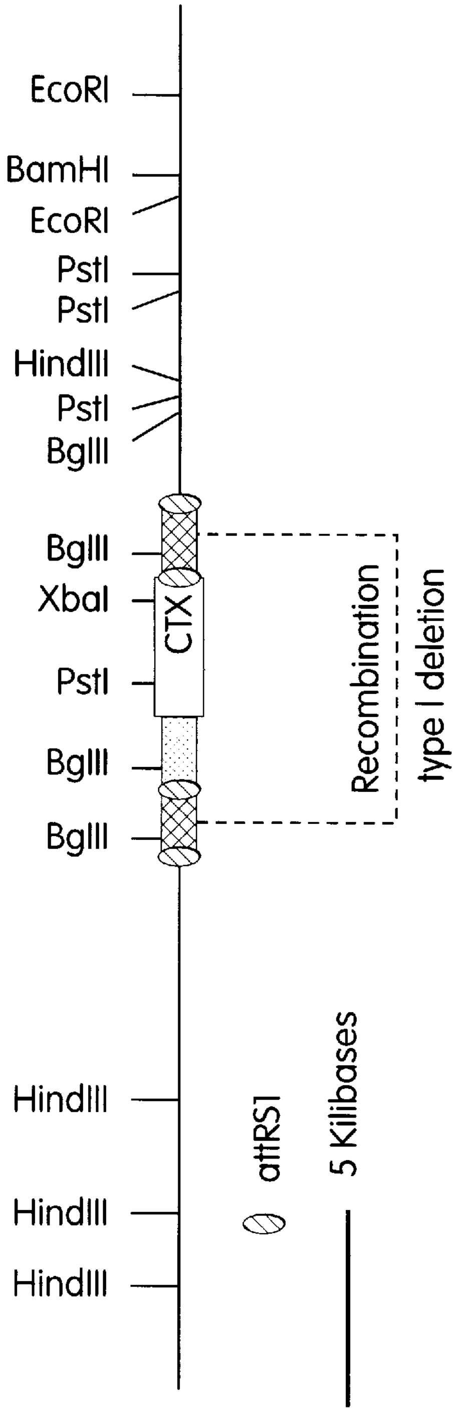
Figure 2B:
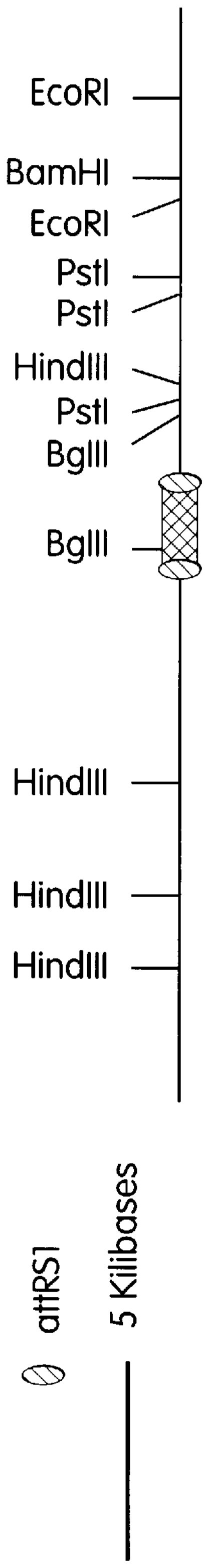
Figure 3A:
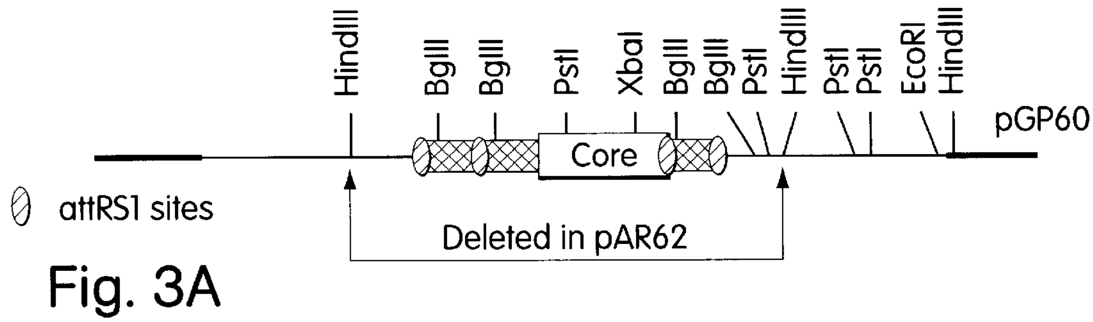
Figure 3B:
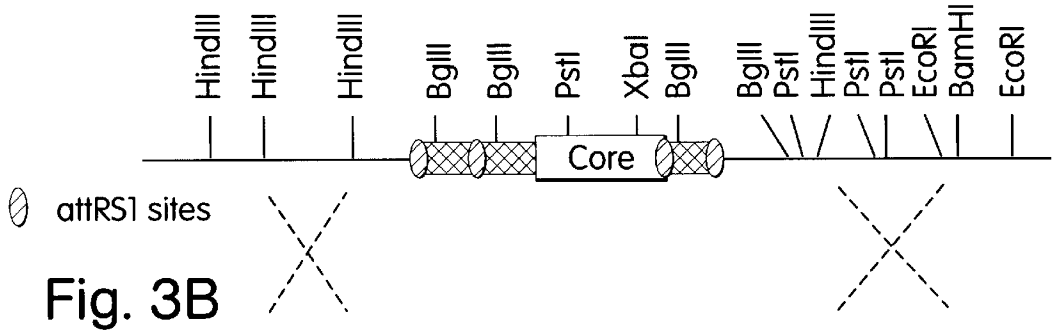
Figure 3C:
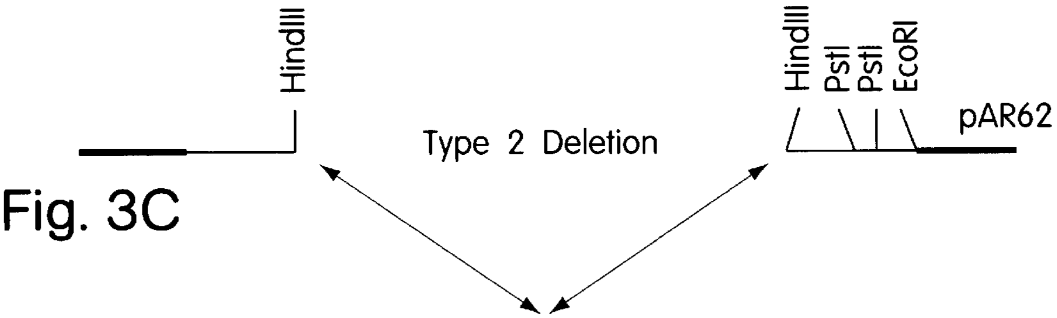
Figure 3D:
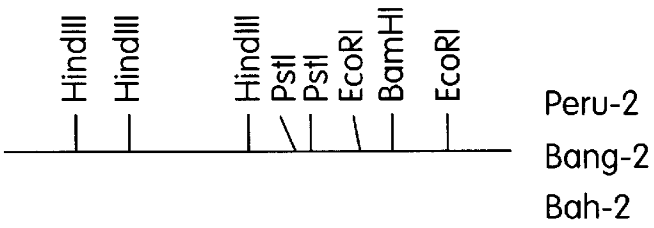

FIGS. 2A and B. (FIG. 2A) Restriction map of the chromosome containing the CTX region from strain C6709-Sm with the CTX element schematically shown as in FIG. 1. Not shown are the restriction maps of strain P27459-Sm and E7946-Sm which are the same except for the variation observed in sites that map within the CTX element's core or RS1 sequences as designated schematically in FIG. 1. (FIG. 2B) Restriction map of corresponding chromosomal region of strain Bang-1, Bah-1, and Peru-1.

FIGS. 3A–D. (FIG. 3A) Restriction map of plasmid pGP60 that carries an inserted DNA fragment corresponding to the chromosome containing the CTX region from strain P27459-Sm with the CTX element schematically shown as in FIG. 1. Below this is a two headed arrow which designates the DNA which has been deleted in plasmid pAR62. (FIG. 3B) The restriction map of the CTX region of strain P27459-Sm is shown including restriction sites that map outside the region cloned on plasmid pGP60. (FIG. 3C) A demonstration of the recombinational events (broken lines) between plasmid pAR62 and the chromosome that produced the Type-2 deletion which gave rise in parental strains C6709-Sm, P27459-Sm and E7946-Sm to deletion mutants Peru-2, Bang-2, and Bah-2, respectively. (FIG. 3D) Restriction map of the chromosome of strains Peru-2, Bang-2, and Bah-2.

Figure 4:
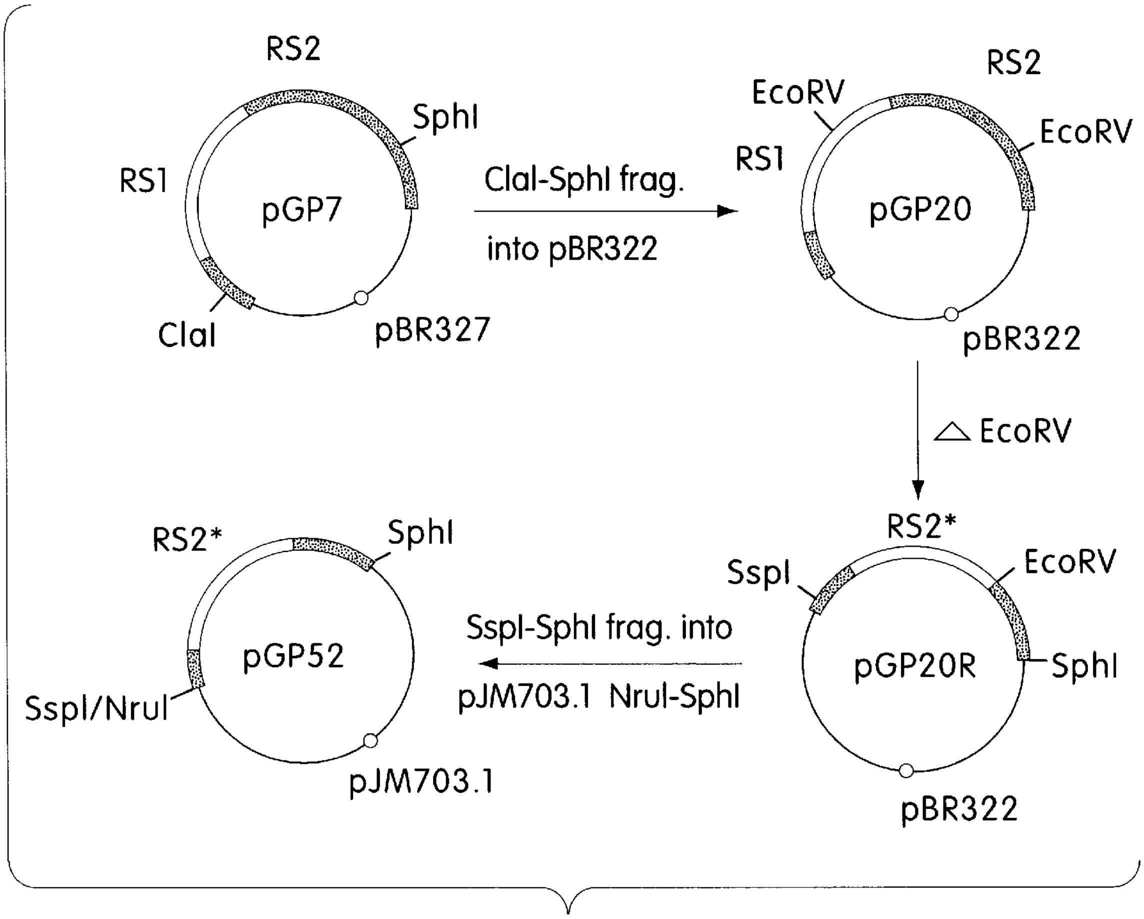

FIG. 4 is a diagrammatical representation of the construction of plasmid pGP52.

Figure 5:
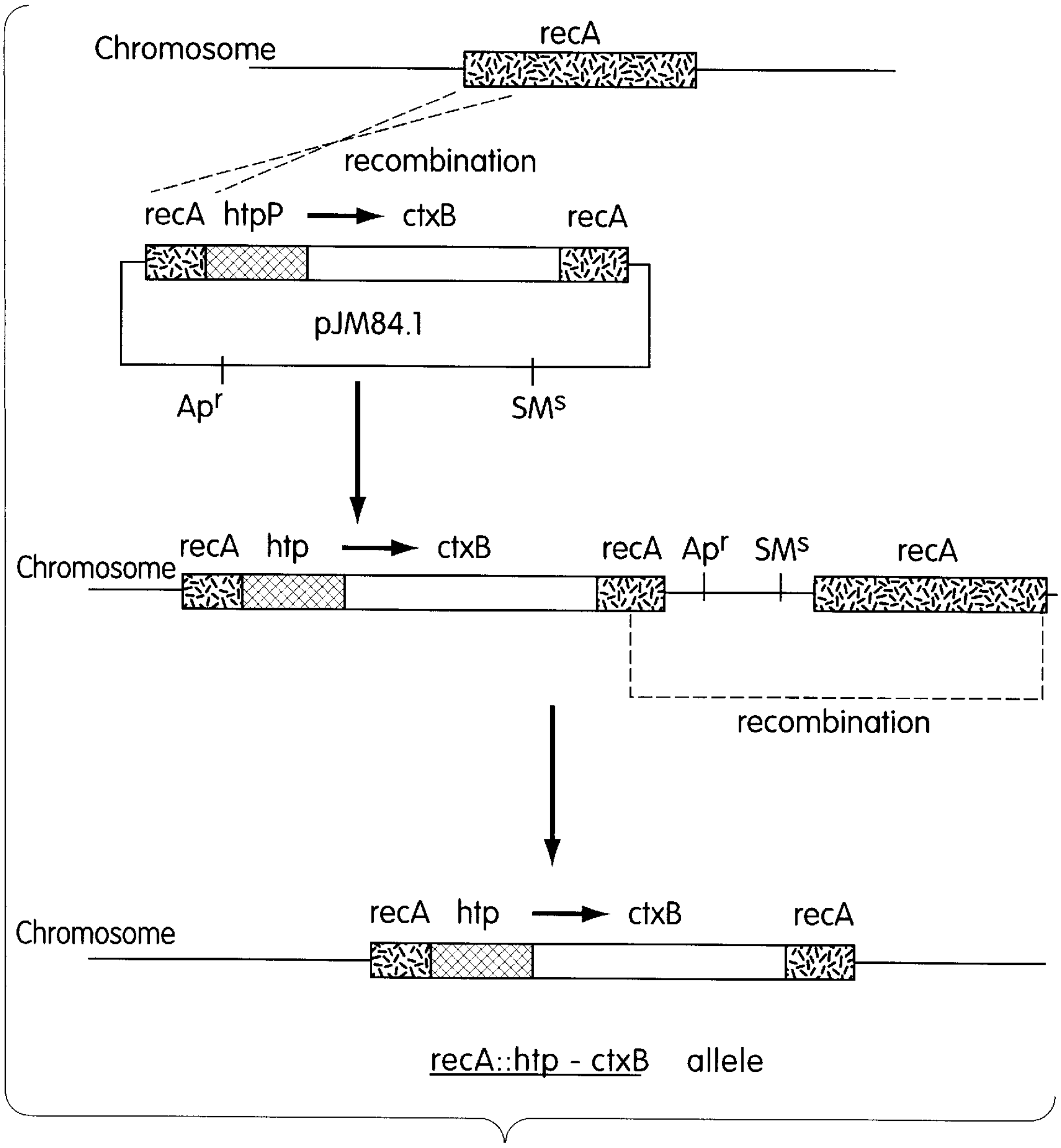

FIG. 5 is a diagrammatical representation of the generation of pJM84.1 and pJM84.2. A 0.6 kb fragment encoding a promoterless B-subunit was generated by PCR. This DNA was ligated into pCR100 and digested with SpeI/EcoRI. The resulting 0.6 kb restriction fragment was ligated into EcoRI/XbaI digested pVC100 and pRT41 vectors, yielding pJM1001 and pJM411, respectively. Each plasmid was digested with BamHI/EcoRI, treated with Klenow, flanked with XbaI linkers, and digested with XbaI. Purified fragments were ligated to XbaI digested pGP84, yielding pJM84.1 and pJM84.2.

Figure 6:
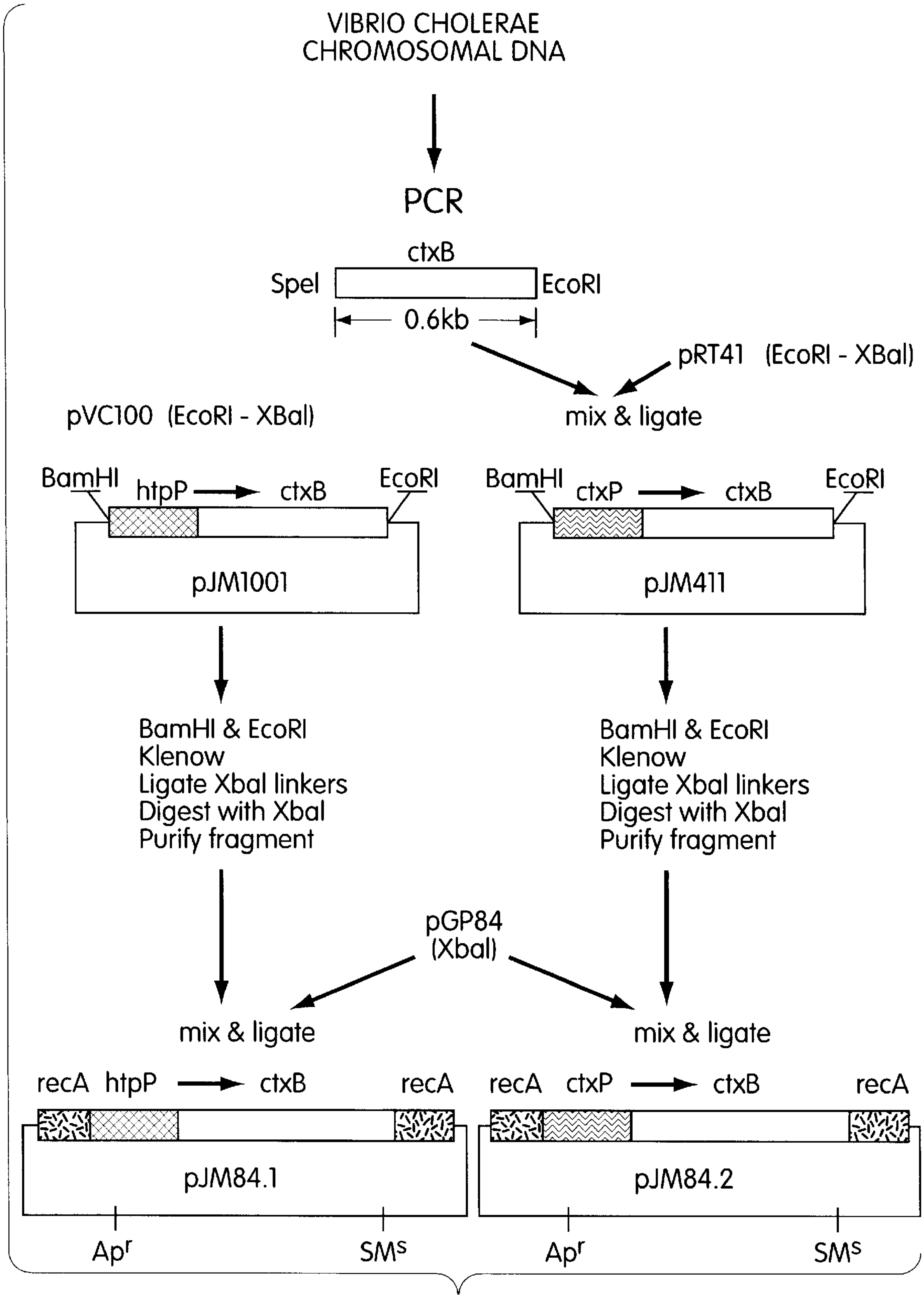

FIG. 6 is a diagrammatical representation of the insertion of the ctxB into the chromosome. Non-replicative pJM84.1 was integrated into Peru-2, Bang-2 or Bah-2 by homologous recombination. Ampicillin resistant recombinant colonies were subsequently plated on medium which contained streptomycin without ampicillin, thus reducing the selective pressure for ampicillin resistance. The resulting ampicillin sensitive colonies were isolated and had selected for excision of DNA flanked by homologous recA DNA sequences.

The invention features attenuated strains of *V. cholerae* that can be used either as live or killed oral vaccines to protect individuals against cholera and potentially other diseases.

Construction of Vaccines

Attenuated derivatives of a *V. cholerae* strain C6709-Sm isolated from a cholera patient in Peru in 1991 have been constructed that can be used as live, oral cholera vaccines. The derivatives Peru-1 and Peru-2, carry small Type-1 (core) and large Type-2 deletions, respectively, which remove the DNA encoding the cholera toxin in addition to DNA encoding zot, an intestinal colonization factor (ICF) that is unrelated to cholera toxin. Because excessive intestinal colonization may be responsible for adverse side effects seen in humans administered earlier prototype live cholera vaccines, the deletion of genes encoding both cholera toxin and ICF in Peru-1 and Peru-2 will render these strains less reactogenic in vaccinees while they retain their immunogenic and therefore protective properties.

The larger Type-2 deletion present in Peru-2 also removes an insertion-like sequence called RS1 which is present in two or more copies as part of a larger DNA segment called the CTX genetic element. The RS1 sequence encodes a site-specific recombination system that can duplicate at a high frequency and cause insertion of the CTX element into the *V. cholerae* chromosome at a 17 base pair target site called attRS1. Sequences nearly identical to attRS1 (and apparently just as recombinationally active) exist at the ends of the RS1 sequences. These sequences are as follows:

attRS1 and flanking chromosomal sequences:

5'-TAAACCTAGAGACAAAATGTTCCTAGTGCG CATTATGTATGTTATGTTAAAT-3'

[SEQ.ID.NO:2]

Left side of RS1 and chromosomal junction:

5'-TAAACCTAGAGACAAAATGTTCCTAGTGCG CATTATGTGGCGCGGCAT . . . RS1 . . . -3'

[SEQ.ID.NO:3]

Right side of RS1 and chromosomal junction:

5'-AAACCCTAGATTCCGCCGCCTTAGTGCGCA TTATGTATGTTATGTTAAAT-3'

[SEQ.ID.NO:4]

The attRS1 and a similar sequence present at the ends of RS1 are underlined. Note that the chromosomal sequence that flanks attRS1 is present on the left and the right side of RS1 with the only overlap being a 17 base pair sequence that is identical to attRS1 on the left end of RS1 and an 18 base pair sequence that matches 17/18 base pairs with attRS1.

Genetically engineered live attenuated cholera vaccines are theoretically safe only if they cannot revert or otherwise regain the capacity to produce cholera toxin. Strains which carry a single copy of the attRS1 sequence can efficiently acquire a new copy of the CTX element through DNA transfer by either P factor conjugation or bacteriophage transduction. Thus, deletions which render *V. cholerae* devoid of RS1 and attRS1 sequences can prevent a vaccine strain from reacquiring the CTX genetic element in nature through its own site specific recombination system. Such a deletion is present in strain Peru-2 and its derivatives.

Six mutant strains of *V. cholerae* with similar but not identical properties have been constructed. Four strains that carry the same two types of deletions (Type-1 and Type-2 ) as strains Peru-1 and Peru-2 were constructed in *V. cholerae* strains isolated from patients in Bangladesh (P27459-Sm) and Bahrain (E7946-Sm). These four derivatives, Bang-1, Bang-2, Bah-1 and Bah-2 are also the subject of the invention because they vary in colonization and/or other properties (e.g., serotype) and they are therefore potentially more suitable than the corresponding Peru strains for use as vaccines in other areas of the world.

Although the smaller Type-1 deletion present in the three strains Peru-1, Bang-l and Bah-1 does not remove all copies of RS1, this particular deletion affects the intestinal colonization properties of some of these strains more severely than the larger deletion present in Peru-2, Bang-2and Bah-2.

Construction of Type-2 Deletion Mutations

A Type-2 deletion removes all sequences corresponding to the CTX genetic element including RS1 sequences and all copies of the attRS1 sequence (FIG. 1). The Type-2 deletion was constructed by recombination between the chromosome of *V. cholerae* and the plasmid sequences cloned on plasmid pAR62 as shown in FIG. 3. Plasmid pAR62 is a derivative of plasmid pGP60 and carries a Type-2 deletion wherein the HindIII fragment shown in FIG. 3 was deleted. Plasmid pGP60 was constructed by first generating a genomic library of strain P27459 by inserting 20–30 kb Sau3A partially digested fragments into the BamHI site of plasmid pLAFR2 (Friedman et al., 1982, Gene 18:289). Colonies were screened by hybridization using probes derived from the ctx region (Mekalanos, 1983, Cell 35:253). A positive colony was picked and the plasmid which was isolated therefrom was named pGP60. Restriction enzyme analysis of this plasmid confirmed that it contained all of the CTX element sequences and additional flanking DNA. Plasmid pAR62 encodes resistance to tetracycline. This plasmid was introduced into a strain of *V. cholerae* by conjugation or electroporation followed by selection on media containing 3 μg/ml of tetracycline. Such a plasmid carrying strain was then screened by colony hybridization with radioactive L-3 probe prepared as described in Goldberg and Mekalanos (J. Bacteriol. 165:723–731, 1986). Colonies carrying the Type-2 deletion inserted into the chromosome did not hybridize to the L-3 probe and surprisingly, occurred at a high frequency (i.e., about 1% of the colonies screened). Southern blot analysis was used to confirm the presence of the expected deletions in these strains.

Construction of Core (Type-1 ) Deletions

A "core deletion" removes only sequences corresponding to the core of the CTX element but leaves behind a copy of the RS1 element on the chromosome (Goldberg et al., J. Bacteriol. 165:723–731, 1986) (FIG. 2.). These deletions occur spontaneously through homologous recombination between RS1 sequences located on the right side and left side of the core region as shown in FIG. 2. Colonies of *V. Cholerae* that contain core deletions can be identified in two ways. First, if the strain carries a selectable marker such as a gene encoding kanamycin resistance inserted in the core region, then the core deletion renders such a strain sensitive to kanamycin (Goldberg et al., J. Bacteriol. 165:723–731, 1986). Second, colonies that contain the core deletion can also be identified by colony hybridization using radioactive CT-1 probe which does not hybridize to strains carrying this deletion (Goldberg et al., J. Bacteriol. 165:723–731, 1986).

By either method, colonies that carry these deletions occurred at a frequency of about 1 per 1000 colonies screened. Analysis by Southern blot hybridization was then used to confirm the expected deletions in these strains.

An Assay for Functional attRS1 Sequences Based Upon Integration of Plasmid pGP52

The plasmid pGP52 is a suicide plasmid which is only capable of replicating in strains of *E. coli* such as SM10λpir (Pearson et al., 1990, Res. Microbiol. 141:893). Plasmid pGP52 was constructed by first digesting the plasmid pGP7 (Mekalanos, 1983, Cell 35:253) with ClaI and SphI. This plasmid contains two RS1 sequences (termed RS1 and RS2) derived from the *V. cholerae* strain E7946-Sm. A fragment of DNA which contained the RS1 sequences was cloned into pBR322 and the resulting plasmid was named pGP20. This plasmid was then digested with EcoRV (which cuts within the RS1 sequences). When this plasmid was religated a new plasmid termed pGP20R was generated containing a hybrid version of RS2 called RS2*, wherein the hybrid RS2 sequences were flanked by core sequences. An SspI-SphI fragment of RS2 was then subcloned into the suicide plasmid pJM703.1 which had been digested with NruI and SphI. The plasmid pJM703.1 is described in Miller et al. (Proc. Natl. Acad. Sci. U.S.A. 81:3471). The resulting plasmid was called pGP52. A diagram depicting the construction of pGP52 is shown in FIG. 4.

When pGP52 is transferred by conjugation into *V. cholerae* strains which contain attRS1 sequences, it integrates into the *V. cholerae* chromosome by means of a site-specific recombination event between the attRS1 sequence on the chromosome and the attRS1 sequence present on the plasmid. Integration events such as these can be quantitated by determining the number of colonies that stably maintain (i.e., are non-selected) ampicillin resistance because resistance to ampicillin is encoded by pGP52. Confirmation of integration can be obtained in Southern blot hybridization experiments. If the *V. cholerae* strain to be tested has functional attRS1 sequences then integration will be observed in the test. If the strain does not contain functional attRS1 sequences, integration will not occur.

In order to assess the ability of the various vaccine candidates to serve as recipients for pGP52, the following experiments were performed. Donor *E. coli* strain SM10λpir pGP52 was mixed with the recipient *V. cholerae* test vaccine strain in 5 ml of Luria broth at concentration of $10^7$ cells from each strain per culture. The mixture was incubated at 37° C. for 5 hours at which time it was diluted 1:100 into fresh Luria broth containing 100 μg/ml of streptomycin. The purpose of the streptomycin is to select against the *E. coli* donor strain by killing it. Thus, only the streptomycin resistant *V. cholerae* recipient strains are capable of growth. This culture was incubated until the growth rate of the cells reached saturation. The cultures were diluted again and further incubated until each cell had replicated a total of 20 times in the absence of any positive selection for pGP52. This culture was then diluted and plated on two separate media compositions in order to quantitate the number of viable colonies. One of these media is Luria broth which does not contain any antibiotics. The number of colonies appearing on these plates represents the total number of cells in the culture. The other medium is Luria broth which contains ampicillin. The number of colonies appearing on these plates represents the number of integration events that occurred following conjugation. The results are expressed as a ratio of stable integration events/total number of viable cells and are presented in Table 1 below.

TABLE 1

Representative Integration Data on Peru Vaccine Strains

| Strain | Stable Integration events/total # viable cells |
|---|---|
| Peru-1 | $5.2 \times 10^{-5}$ |
| Peru-2 | Not detectable ($<5 \times 10^{-8}$) |
| Peru-3 | Not detectable ($<5 \times 10^{-8}$) |
| Peru-4 | Not detectable ($<5 \times 10^{-8}$) |
| Peru-5 | Not detectable ($<5 \times 10^{-8}$) |

Based on these data it is evident that strain Peru-1, which contains two copies of the attRS1 sequences is capable of integrating the plasmid pGP52 into its chromosome at a frequency that is at least 1000-fold higher than any of the other strains tested, all of which lack any attRS1 sequences.

Serological Characterization of Vaccine Strains

The vaccine strains Peru-2, Bang-2, and Bah-2 were characterized further in terms of their serological and colonization properties. The data presented in Table 2 demonstrate that each derivative retained its expected serotype (i.e., the serotype of each of the mutants respective parental strain) when freshly harvested bacterial cells were tested by slide agglutination using Difco *V. cholerae* 01 Inaba or Ogawa typing serum. This result indicates that these strains still express LPS antigens. Other tests demonstrate that these mutant strains are motile, prototrophic, and still express Tcp pili. Thus, the mutants express a number of properties that are important for their ability to be useful as live vaccine strains.

Colonization Properties of the Vaccine Strains and Core Deletion Mutants

To test the colonization properties of these vaccine strains, a mouse intestinal competition assay was used as described in Taylor et al. (Proc. Natl. Acad. Sci. U.S.A. 84:2833–2837, 1987) which has been shown to correlate accurately with the colonization properties of mutant strains when they are subsequently tested in human volunteers (Herrington et al., J. Exper. Med. 168:1487–1492, 1988). The assay measures differences in colonization of a mutant strain by comparing its ability to compete for growth and survival with another closely related or isogenic strain. In this assay, the mutant and competing strains were mixed in a ratio of approximately 1:1 and then approximately one million cells of this mixture were introduced to the stomach of 3–5 day old suckling CD-1 mice. After 24 hours, the mice were sacrificed, the intestine was dissected, homogenized, and plated on bacteriological media containing streptomycin which selects for both strains. Colonies that grew after overnight incubation are then tested for additional markers which differentiate the mutant strain from the competing strain (i.e., resistance to kanamycin or hybridization with appropriate radioactive DNA probes; see legend of Table 3).

As shown in Table 3, Bang-2, and Bah-2 both exhibited a mild intestinal colonization defect that resulted in approximately 4–13 fold greater recovery of the isogenic competing strains than the mutant strains after 24 hours of growth in the mouse intestine. Also shown in Table 3, are results from competition assays involving core deletion mutant strains Peru-1, Bang-1 and Bah-1. Like the Type-2 deletion strains Bang-2and Bah-2, these core deletion mutants were defective in colonization relative to their isogenic competing strains. Because core deletions remove sequences corresponding to the core of the CTX element (FIGS. 1 and 3), these data suggest that the core of CTX element encodes an "intestinal colonization factor, or ICF". Cholera toxin by itself is not an ICF. Strains SM44 and SM115 which are defective in cholera toxin production due to a deletion in the ctx genes and insertion of a gene encoding kanamycin resistance as described in Goldberg and Mekalanos (J. Bacteriol. 165:723–731, 1986) outcompete their respective mutant strains (Bang-1, Bang-2 and Bah-1, Bah-2) in the intestinal competition assay. Thus, it is apparent that SM44 and SM115 make ICF even though they do not produce cholera toxin, while the mutants do not. Furthermore, because the CTX core region was the only DNA that is deleted in both core as well as Type-2 deletions and mutants carrying both types of deletions were similarly defective in colonization, it can also be concluded that ICF is encoded by the core region of the CTX element as shown in FIG. 1.

Recently, a new toxin called ZOT has been found to be encoded by the core region (Baudry et al., 1992, Infect. Immun. 60:428–434). We have evidence that mutations in the ZOT gene do not produce the colonization defect observed in Type-1 or Type-2 deletion mutants. Accordingly, ICF is designated as a separate and distinct property from ZOT. The vaccine strains described herein carrying Type-1 or Type-2 deletions are defective in ICF.

In contrast, strain Peru-2 exhibited no significant defect in intestinal colonization relative to its competing strain C6709-Sm (Table 2). However, the total cell yield of either strain C6709-Sm or Peru-2 in the mice was typically 10–100 fold less than strains SM44 or SM115, suggesting that the present in strains Peru-2, Bang-2and Bah-2 assures that the genes for ICF cannot reactivate and become functional in the vaccine derivatives. The Type-2 deletion of ICF genes apparently causes a mild colonization defect. Such may be useful as an attenuating mutation in cholera vaccine development, because wild type ICF may be responsible for undesirable levels of toxicity.

TABLE 2

Properties of Mutant Strains

| Mutant Strains | Parental Strain* | Serotype | Type of Deletion |
|---|---|---|---|
| Peru-2 | C6709-Sm | Inaba | Type-2 |
| Bang-2 | P27459-Sm | Ogawa | Type-2 |
| Bah-2 | E7946-Sm | Inaba | Type-2 |

*Note that the designation "Sm" behind the strain name refers to streptomycin resistance. This is a spontaneously selected strain which is resistant to 100 μg/ml of streptomycin and was the result of a spontaneous point mutation in the gene for a ribosomal protein. This resistance marker is not associated with a plasmid or transposon and is therefore not transmissible to enteric flora. Because all mutant strains are derived from the indicated parental strains, all mutant strains are also resistant to streptomycin.

TABLE 3

Infant Mouse Competition Assays[a]

| Mutant Strain | Competing Strain | Input Ratio Mutant/Competing Strain | Output Ratio Mutant/Competing Strain |
|---|---|---|---|
| Bang-2 | SM44[b] | 0.61 | 0.16 |
| Bah-2 | SM115[c] | 0.92 | 0.07 |
| Peru-2 | C6709-Sm[d] | 0.74 | 0.65 |
| Bang-1 | SM44[b] | 0.85 | 0.05 |
| Bah-1 | SM115[c] | 0.61 | 0.04 |
| Peru-1 | C6709-Sm[d] | 0.89 | 0.94 |

[a]Infant mouse colonization assays were performed according to the method described in Taylor et al. (Proc. Natl. Acad. Sci. USA. 84: 2833–2837, 1987). The ratio of strains was determined by either differential sensitivity to antibiotics or by colony hybridization with appropriate probes as described in the additional footnotes below.

[b]Strain SM44 has been described in Goldberg and Mekalanos (J. Bacteriol. 165: 723–731, 1986) and is a kanamycin resistant derivative of the parental strain P27459-Sm. The gene encoding kanamycin resistance in SM44 was inserted in the cts locus. Because Bang-1 and Bang-2 were derivatives of P27459-Sm competition with SM44 measures colonization differences that can be attributed to the effect of the Type 2 rather loss of ctx. Strains Bang-1 and Bang-2 were sensitive to kanamycin and were differentiated from SM44 in these competitions assays by scoring colonies for resistance to 30 μg/ml kanamycin.

[c]Strain SM115 has been described in Goldberg and Mekalanos (J. Bacteriol. 165: 723–731, 1986) and is the kanamycin resistant derivative of the parental strain E7946-Sm. The gene encoding kanamycin resistance in SM115 was inserted in the ctx. locus. Because Bah-1 and Bah-2 are derivatives of P27459-Sm competition with SM115 measures colonization differences that can be attributed to the effect of the Type 2 deletion rather than loss of ctx. Strains Bah-1 and Bah-2 were sensitive to kanamycin and were differentiated from SM115 in these competitions assays by scoring colonies for resistance to 30 μg/ml kanamycin.

[d]Strain C6709-Sm is the parental strain of Peru-1 and Peru-2. Peru-2 carries a Type −2 deletion while Peru-1 carries a core deletion. Both these deletions remove the ctx genes and thus both Peru-1 and Peru-2 were negative in colony hybridization blots when probed with the CT-1 probe described in Goldberg and Mekalanos (J. Bacteriol. 165: 723–731, 1986) while strain C6709-Sm was positive using the same probe. Thus, both Peru-1 and Peru-2 were differentiated from C6709-Sm in these competitions assays by scoring colonies for hybridization with the CT-1 probe.

Peru strain C6709-Sm and its derivative Peru-2 may already carry an undefined colonization defect. Since deletion of the core of all or part of the CTX element did not cause a further defect in the colonization of either strain Peru-1 or Peru-2, it can be concluded that strain C6709-Sm is partially defective in ICF already even though it carries DNA sequences that correspond to the CTX core region. Deletion of the entire CTX region as defined by the Type-2 mutations The mutant strains described can be further improved as vaccine candidates by creating additional mutations within each strain that will serve to enhance the safety and immunogenicity of the vaccine.

With regard to safety, a second mutation can be introduced into the recA gene of any of the strains described above, which mutation is designed to inactivate that recA gene. Such double mutant strains will therefore be defective in recombination and will be unable to recombine with wild type strains of *V. cholerae* in the environment. Thus, they will be incapable of acquiring wild type toxin genes and expressing the CTX element. Immunogenicity can also be improved by introducing additional mutations into each strain which will allow that strain to express cholera toxin related antigens (e.g., the B subunit of cholera toxin) or other heterologous antigens, e.g., the nontoxic B subunit of Shiga-like toxin or various CFA antigens of enterotoxigenic *E. coli* strains, Shiga-toxin, anthrax toxin, Pseudomonas endotoxin A, pertussis toxin, tetnus toxin; antigens from Herpes virus, rubella virus, influenza virus, mumps virus, measles virus, poliomyelitis virus, antigenic fragments from the HIV capsid; and immunogenic polypeptides from eukaryotic parasites causing malaria, pneumocystis pneumonia, and toxoplasmosis (Karjalainen et al., 1989, Infect. Immun. 57:1126; Perez-Casal et al., 1990, Infect. Immun. 58:3594). Thus, a series of mutated derivatives can also be useful in the invention, each incorporating additional properties that render the strains safer, genetically more stable and more broadly immunogenic. The construction of such derivatives is described below.

Construction of recA/ctxB Alleles

Cholera toxin B subunit is known to be a nontoxic, highly immunogenic molecule that is capable of inducing cholera toxin neutralizing antibodies. In order to generate more immunogenic vaccine strains, a new copy of the ctxB gene was introduced into the vaccine strains containing the Type-2 deletions described above (because Type-2 deletions remove all of the coding sequence for the cholera toxin B subunit). This was accomplished in a series of steps that are described below.

First, a promoterless copy of the ctxB gene was constructed using the polymerase chain reaction (PCR). For PCR, the downstream primer was designed so that the ctxB coding sequence could be synthesized in such a way as to eliminate the attRS1 site that lies just downstream from the stop codon in the ctxB gene. This primer had the following sequence: 5'-GGGCTAAAGTTAAAAGACAAA TATTTTCAGGC-3' [SEQ.ID.NO:5]. The upstream primer was designed so that only the last 24 carboxyterminal amino acid residues of the A2 subunit could be encoded by the product of the reaction. This primer had the following sequence: 5'-GGGTAGAAGTGAAACGGGGTTTACCG-3' [SEQ.ID.NO:6]. All other nucleotides in the DNA encoding the A subunit were excluded from the reaction. The DNA encoding the carboxyterminal amino acids of CtxA2 were retained in the final product to allow for translational coupling of ctxB gene expression. Since the toxic activity associated with cholera toxin is derived from the CtxA1 polypeptide, all sequences encoding the A1 polypeptide were excluded from the PCR reaction.

PCR was performed using the ctxB primers as described above using *V. cholerae* DNA from the Peruvian strain, C6709-Sm (FIG. 5). The product of the reaction, a 0.6 kilobase pair fragment, was cloned into plasmid pCR100. This fragment was then cut out of the plasmid as a 0.6 kilobase pair SpeI-EcoRI fragment and was cloned into two individual acceptor plasmids, XbaI-EcoRI digested pRT41 and XbaI-EcoRI digested pVC100. The resulting plasmids, pJM411 and pJM1001, then each encode a copy of the ctxB gene under the control of either the ctx promoter (ctxP) or the htpG promoter (hptP) of *V. cholerae*, respectively. These plasmids were then transferred to the nontoxigenic strain *V. cholerae* 0395-NT (Mekalanos et al., 1983, Nature 306:551 and U.S. Pat. No. 4,935,364), generating two new strains termed 0395-NT pJM411 and 0395-NT pJM1001. The amount of cholera B subunit produced by each strain was measured by GMI ELISA. Strain 0395-NT pJM411 produced 30 $\mu$g/ml, while strain 0395-NT pJM1001 produced 100 $\mu$g/ml in LB culture supernatant fluids. These results demonstrate that the PCR product was a functional ctxB gene encoding an antigenic cholera B subunit capable of binding to ganglioside GMI and was therefore similar to that secreted by normal wild type *V. cholerae.*

In the next step, EcoRI-BamHI fragments of DNA specifying the promoter-ctxB constructs were subcloned into the suicide recA plasmid pGP84. This plasmid contains a *V. cholerae* chromosomal DNA insert that corresponds to the DNA which flanks the recA gene of *V. cholerae* (i.e., an internal deletion of recA). Plasmid pGP84 is a derivative of suicide plasmid pJM703.1 (Miller et al., 1988, J. Bacteriol. 170:2575) and encodes sequences corresponding to the flanking regions of the recA gene of *V. cholerae* (Goldberg et al., 1986, J. Bacteriol. 165:715) including a BglII-PvuII fragment on the left side and an XbaI-EcoRI fragment on the right side. A 1.3 kb fragment encoding kanamycin resistance is positioned between these two fragments. Plasmid pGP84 also contains a NruI-BamHI fragment encoding sensitivity to streptomycin. This latter fragment is derived from plasmid pNO1523 (Dean, 1981, Gene 15:99). When pGp84 is digested with XbaI, the 1.3 kb fragment is removed and other XbaI fragments can be inserted into this deleted recA region.

The subcloning was accomplished as follows: Each of the two EcoRI-BamHI fragments specifying the promoter-ctxB constructs were modified by the addition of XbaI linkers. They were individually ligated to XbaI digested pGP84 to generate two new plasmids pJM84.1 and pJM84.2, each of which contains DNA specifying the htpP-ctxB and the ctxP-ctxB constructs respectively (FIG. 6).

Next, plasmids pJM84.1 and pJM84.2 were transferred into *V. cholerae* strains Peru-2, Bang-2and Bah-2 and ampicillin resistant colonies were selected. Because these plasmids are incapable of replication in *V. cholerae*, they integrate into the host cell chromosome by homologous recombination generating the structure shown in FIG. 6. Both plasmids also encode a gene for streptomycin sensitivity which allows for positive selection against a plasmid integration event in strains that are streptomycin resistant (i.e., strains Peru-2, Bang-2 and Bah-2). Thus, when strains that have a plasmid integrated into the chromosomal DNA are grown on medium containing 2 mg/ml streptomycin, colonies that have reverted to ampicillin sensitivity can be isolated. Strains that had now crossed out the integrated plasmid in such a way as to leave behind the recA deletion mutation together with the ctxB construct were then selected from among these latter strains. These strains were easily identified as having the following properties:

1. They were ampicillin sensitive.
2. They were killed in the presence of 0.1 ml methyl methane sulfonate per ml of LB, a characteristic phenotype of $recA^-$ cells.
3. They produced the cholera B subunit as measured by GMI-ELISA.
4. Southern blot analysis using recA and ctxB probes confirmed that they contained DNA fragments consistent with the presence of the ctxB construct and deletion of the appropriate recA sequences.

Bacterial strains that were isolated following the procedure described above are as follows:

| STRAIN | GENOTYPE |
|---|---|
| Peru-3 | attRS1 deletion, recA::htpP-ctxB, str |
| Peru-4 | attRS1 deletion, recA::ctxP-ctxB, str |
| Bang-3 | attRS1 deletion, recA::htpP-ctxB, str |
| Bah-3 | attRS1 deletion, recA::htpP-ctxB, str |
| Bah-4 | attRS1 deletion, recA::ctxP-ctxB, str |

Construction of lacZ-ctxB Alleles

The recA mutation contained within the vaccine strains described above renders the strains deficient in homologous recombination. In order to produce candidate vaccines that were still capable of homologous recombination, the ctxB gene was inserted into the lacZ gene of *V. cholerae* as described below.

The plasmid pCG698 which encodes the lacZ gene of *V. cholerae*, contains a unique HpaI site in the middle of the lacZ coding sequence. The plasmid pCG698 was constructed as follows: The β-galactosidase gene of *V. cholerae* was cloned from a library of chromosomal DNA fragments from strain E7946 as described (Mekalanos, 1983, Cell 35:253). It was found to express β-galactosidase and following restriction enzyme mapping, was found to contain a 6 kb insert containing 2 HpaI sites in the lacZ gene each of which was separated by 2.1 kb of DNA. This plasmid was linearized with HpaI and XbaI linkers were ligated to the ends. An EcoRI-BamHI fragment containing the ctxP-ctxB construct was removed from pJM411 as described above, the ends were modified by the addition of XbaI linkers and the fragment was ligated into the similarly modified pCG698. The resulting plasmid pJM6891, now contained the ctxP-ctxB construct inserted into the middle of the lacZ gene. This plasmid was transferred into *V. cholerae* strains Peru-2, Bang-2and Bah-2 and each resulting strain was screened for growth in the presence of X-gal. White colonies containing an inactivated lacZ gene were picked and purified. Strains that contained an integrated copy of the lacZ::ctxP-ctxB sequences into the host cell chromosome were obtained by curing the bacteria of pJM6891 by growth in the absence of ampicillin. The presence of the appropriate sequences was confirmed by Southern blot analysis and the ability of these bacteria to produce cholera toxin B subunit was confirmed by GMI-ELISA. Bacterial strains isolated following this procedure are as follows:

| STRAIN | GENOTYPE |
|---|---|
| Peru-5 | attRS1 deletion, lacZ::ctxP-ctxB, str |
| Bang-5 | attRS1 deletion, lacZ::ctxP-ctxB, str |
| Bah-5 | attRS1 deletion, lacZ::ctxP-ctxB, str |

In order to characterize some of these carrier cholera vaccine candidates with regard to mouse colonization, mice were infected with the strains listed below. The strain TCP2, a derivative of 0395-N1 which contains a TcpA deletion and does not colonize the intestine of human volunteers, served as a control. Five mice were used for each strain. At 24 hours post-infection, the upper intestine was removed from each mouse, homogenized and assayed for the number of *V. cholerae* present using a simple plating assay. The results are presented in the table below. Essentially, no TCP2 bacteria were detected in the intestines of mice infected with TCP2 and thus the values given below represent the number of bacteria of each strain that colonized the mouse intestine above a background level of zero.

| Strain | CFU per mouse[a] | Genotype/Construct[b] |
|---|---|---|
| Peru-3 | $9.4 \times 10^5$ | attRS1 deletion #2, recA::htpG-ctxB |
| Peru-2 | $2.5 \times 10^6$ | attRS1 deletion #2, |
| Peru-4 | $6.0 \times 10^6$ | attRS1 deletion #2 recA::ctx-ctxB |
| Peru-5 | $6.6 \times 10^6$ | attRS1 deletion #2 lacZ::ctx-ctxB |
| Peru-2 | $9.9 \times 10^6$ | attRS1 deletion #2, |
| Bang-3 | $2.7 \times 10^7$ | attRS1 deletion #2, recA::htpG-ctxB |

[a]Colony forming units recovered per mouse (average of five mice).
[b]The construct attRS1 deletion #2 is a Type 2 deletion constructed with plasmid pAR62, described in FIG. 3.
The construct recA::htpG-ctxB is a deletion of the recA gene and insertion of the *cholera* toxin B subunit gene under control of the heat shock promotor derived from the htpG of *V. cholerae*.
The construct recA::htpG-ctxB is a deletion of the recA gene and insertion of the *cholera* toxin B subunit gene under control of the cholera toxin promoter derived from the ctx gene of a hypertoxigenic strain 569B of *V. cholerae*.
The construct lacZ::ctx-ctxB is an insertion in the lacZ gene of *V. cholerae* that is composed of the *cholera* toxin B subunit gene under control of the cholera toxin promotor derived from the ctx gene of a hypertoxigenic strain 569B of *V. cholera*.

The results suggest that the presence of the recA::htpP-ctxB allele serves to reduce the ability of the Peru-derived strains to colonize the intestine (compare, for example, Peru-3 with Peru-2). However, the effect of this construct on colonalization of the Bang-derived strain was less marked (compare Bang-3 with Bang-2). In general, introduction of the constructs wherein ctxB is under the control of its own promoter had less effect on colonalization that the constructs wherein it was placed under the control of the heat shock promoter. It should be noted that strains Peru-2, Peru-3 and Bang-3 vary in their colonalization properties over a 28-fold range. It is well within the art following the protocols described above, to isolate additional vaccine candidates that vary even more widely in their colonalization properties.

In summary, the data demonstrate the feasibility of using genetic engineering techniques to generate novel ctxB-containing *V. cholerae* strains wherein the expression of the ctxB gene is placed under the control of either of two *V. cholerae* promoters (ctxP and htpP). The engineered genes can be recombined into the *V. cholerae* chromosome into target genes such as recA or lacZ to generate strains which stably express large amounts of cholera toxin B subunit (for example, strains Peru-3, Peru-4 and Peru-5).

Isolation of spontaneous soft agar penetration-defective strains of *V. cholerae*

Mutants of *V. cholerae* which are defective in soft agar penetration can be useful in the production of vaccines. The rational for utilizing these mutants is as follows. The mucous layer of the intestine is thought to be viscous and mutants defective in penetration of soft agar might be deficient in penetration of this mucous. Al though defective in penetration through mucous, these mutants may still present antigen to the Peyer patches which are not covered by a thick mucous gel and which include antigen-sampling cells specific for IgA antibody production. As a result, penetration defective mutants are predicted to have low reactogenecity, yet be highly antigenic, and these characteristics are desirable for a live vaccine. Although non-motile mutants are one class of mutants defective in penetration of soft agar, other types of mutations may also result in a soft agar penetration-defective phenotype (i.e., a swarming phenotype) and may be useful for vaccines. In keeping with this line of reasoning, completely non-motile mutants, i.e., mutants unable to swarm in agar-free media, may be useful candidate vaccines.

To obtain such mutants, soft agar can be used to assess the ability of bacteria to penetrate a media of high viscosity (soft agar media which is 0.25–0.4% agar), as described below. One such soft agar penetration-defective vaccine with a high therapeutic value is Peru-14.

Peru-14 is soft agar penetration-defective, and, in addition, over 50% of Peru-14 cells are fillamentous, with a spiral-like appearance and having a cell length of greater than 5 normal cell lengths (25 nM, as opposed to the wild-type cells length of 5 nM).

Peru-14 was isolated as a soft agar penetration-defective derivative of the triply-deleted Peru strain (Peru-3) (ctxA$^-$, att$^-$, and recA$^-$) that was free from side effects but still retained the ability to colonize vaccinees as shown in below (Table 7).

Although Peru-14 was isolated based upon the theory stated above, this theory of function may or may not accurately and completely explain the effectiveness of Peru-14 as a vaccine. The usefulness of Peru-14 as an effective vaccine does not depend on the correctness of this theory.

TABLE 7

Outcome of Immunization with Freshly Harvested Peru-14 Cholera Vaccine

| Dose (cfu) day | Volunteer # | Symptoms | Stool | Duration of Excretion (days)/Peak |
|---|---|---|---|---|
| 2 × $10^6$ | 28 | Gas | | Formed |
| 3/3 | 29 | Cramps | | Formed |
| 14/2 | 30 | None | | Formed |
| — | 33 | None | | Formed |
| 4/4 | 34 | None | | 336 g* |
| 4/1 | 35 | None | | Formed |
| 3/3 | | | | |
| 9 × $10^8$ | 25 | None | | Formed |
| 25/1 | 26 | Gas | | Formed |
| 3/1 | 27 | Headache | | Formed |
| 2/2 | 31 | Nausea, Loss of Appetite | | Formed |
| 7/4 | | | | |
| 5/3 | 32 | None | | Formed |
| 33/1 | 36 | Cramps | | 63 g+ |

*Volunteer had painless semi-solid stool at 72 hours post-immunization. Stool was culture-negative for Peru-14.
+ Volunteer had two small liquid stools at 48 hours post-immunization. Stools were culture-positive for Peru-14.

Specifically, the Peru-14 soft agar penetration-defective defective strain was produced as follows. Peru-3 was grown overnight in LB broth containing 100 μg streptomycin sulfate at 30° C. The culture was diluted to approximately 2000 cfu/ml and 0.1 ml was plated onto LB plates containing 100 μg streptomycin. After incubating the plates overnight at 30° C., approximately 1000 colonies were toothpicked into soft agar plates (LB broth+0.45% Bacto-agar) and incubated overnight at 30° C. The inoculating toothpick is inserted only 1–2 mm into the surface of the soft agar plate. Of the 1000 colonies picked, 25 appeared to be non-penetrating. Non-penetrating isolates appear as colonies of approximately 2 mm in diameter, whereas penetrating isolates swarm on and within agar the agar to a diameter greater than 5 mm. These colonies were repicked into soft agar once again, along with a known non-penetrating, non-motile cholera strain and the original Peru-3 strain. One colony of the 25 was non-soft agar penetrating (when compared to the controls). This colony, designated Peru-14, was still Inaba positive with agglutination sera, and produced the same level of B-subunit toxin as Peru-3 when tested in the B-subunit ELISA. The methods described above can be used for isolating soft agar penetration defective mutants of any *V. cholerae* strain. Non-revertable penetration-defective mutants, such as those harboring a genetic deletion, can be made using the methods described above.

Bengal strains

A highly unusual non-01 virulent strain has recently been discovered to be responsible for a cholera epidemic on the Indian sub-continent. Survivors of earlier 01 serogroup epidemics are not immunologically protected against this strain.

This strain has been deposited with the American Type Culture Collection (ATCC) in Rockville, Md. Bengal can be attenuated as described above for the other strains, e.g., by one or more of the following mutations: ctx$^-$, att$^-$, or recA$^-$, or a soft agar-defective phenotype, Bengal-2 ("Beng-2") and Bengal-3 ("Beng-3"), are genetically equivalent to Peru-2 and Peru-3. Such an attenuated Bengal strain may be combined with one of the above-described attenuated Peru strains to provide a dual or multi-cholera strain vaccine.

Human testing of Peru-3 and Peru-5

Human studies of the efficacy of Peru-3 and Peru-5 were performed as follows.

Blood samples were drawn from volunteers prior to immunization and at 7, 14, 21, and 28 days post immunization. The *V. cholerae* antibodies in their blood stream were measured and levels are shown in Table 4. The immunogenecity of vaccine prototypes Peru-3 and Peru-5 were evaluated in human volunteer studies. Volunteers ingested freshly harvested Peru-3 or Peru-5 at 3 different doses in 100 ml of 10% sodium bicarbonate. Peru-3 and Peru-5 were also shown to induce antitoxin antibodies (Table 5). In addition, Peru-3 and Peru-5 were shown to protect volunteers from challenge with a wild-type El Tor *V. cholerae* (strain N16961, Table 6). We conclude that Peru-3 in particular provokes a potent immune response (Tables 4 and 5) and confers protection from cholera in human studies (Table 6).

TABLE 4

Vibriocidal Titers After Immunization with Peru-3 or Peru-5 (July 1992)

| Strain (cfu) | Volunteer | Pre | 7 | 14 | 21 | 28 | Peak |
|---|---|---|---|---|---|---|---|
| Peru-3 (4 × $10^6$) | 1 | 50 | 1600 | 6400 | 6400 | 6400 | 6400 |
| | 2 | <100 | 50 | 100 | 50 | 100 | 100 |
| | 5 | <100 | 1600 | 6400 | 400 | 400 | 6400 |
| Peru-3 (1 × $10^8$) | 7 | <100 | 400 | 1600 | 400 | 400 | 1600 |
| | 12 | <100 | 400 | 800 | 400 | 200 | 800 |
| | 13 | <100 | 3200 | 6400 | 3200 | 1600 | 6400 |
| Peru-5 (2 × $10^6$) | 11 | <100 | 1600 | 6400 | 3200 | 6400 | 6400 |
| | 14 | <100 | 200 | 6400 | 3200 | 1600 | 6400 |
| | 15 | <100 | 800 | 6400 | 1600 | 3200 | 6400 |

Heat activated serum samples were serially diluted into microtiter wells, mixed with log phase *V. cholerae* (final concentration of 5 × $10^7$) and guinea pig complement (final concentration of 11%) and incubated at 37° C. for 1 hour.
Brain-Heart-Infusion broth was then added to plates and incubated at 37° C. for 2.75 hours. Values in table represent the reciprocal titers at which antibody-mediated killing of *V. cholerae* was 50% or greater.

TABLE 5

Cholera Antitoxin Titers after immunization with Peru-3 or Peru-5 (July 1995)

| Strain (cfu) | Volunteer | .2 | 7 | 14 | 21 | 28 | Peak Increase (fold) |
|---|---|---|---|---|---|---|---|
| Peru-3 (4 × $10^6$) | 1 | 8 | 8 | 32 | 32 | 32 | 4 |
| | 2 | <2 | <2 | <2 | <2 | <2 | None |
| | 5 | 2 | 64 | 64 | 2 | 256 | 14 |

TABLE 5-continued

Cholera Antitoxin Titers after immunization with Peru-3 or Peru-5 (July 1995)

| Strain (cfu) | Volunteer | .2 | 7 | 14 | 21 | 28 | Peak Increase (fold) |
|---|---|---|---|---|---|---|---|
| Peru-3 ($4 \times 10^8$) | 7 | 2 | 2 | 4 | 4 | 4 | 2 |
| | 12 | <2 | 2 | 4 | 4 | 4 | 4 |
| | 13 | <2 | <2 | <2 | <2 | <2 | None |
| Peru-5 ($2 \times 10^6$) | 11 | 4 | 4 | 4 | 4 | 4 | None |
| | 14 | 2 | 2 | 2 | 2 | 2 | None |
| | 15 | 8 | 8 | 8 | 8 | 8 | None |

Serum samples were serially diluted into pre-treated, ganglioside/*cholera* toxin B-subuin coated 96 well microtiter plates and incubated at 37° C. for 30 minutes. Following 3 washes with PBS, goat anti-human antibody-alkaline phosphatase conjugate (1/1000) was ackled and incubated at 37° C. for 30 minutes. Following 3 washes with PBS, 2 mg/ml PNPP was added to each well and incubated for 15 minutes. Reaction was stopped with 0.1M $K_2PO_4$ and read at an O.D. of 405 nm. Values on the table represent the reciprocal titers and the increase of day-2 compared to peak titer.

TABLE 6

Outcome for Volunteers Challenged with $2 \times 10^6$ cfu *Vibrio cholerae* (N16961) wild-type Organisms (November 1992)

| Subject Number | Previous Vaccination | Initial Dose | Symptoms | Diarrhea (grams) | Onset of Symptoms |
|---|---|---|---|---|---|
| 1 | Peru-3 | 6 logs | None | Formed | |
| 2 | Peru-3• | 6 logs | Tired, gurgling | 534 | 18–48 hours |
| 5 | Peru-3 | 6 logs | None | 3 | |
| 7 | Peru-3 | 8 logs | None | 23 | 36 hours |
| 11 | Peru-5 | 6 logs | None | Formed | |
| 12 | Peru-3 | 8 logs | None | Formed | |
| 14 | Peru-5 | 6 logs | None | Formed | |
| 15 | Peru-5 | 6 logs | None | Formed | |
| 22 | Control | | T 100.7 F, HA, nausea LOA, gurgling, cramps | 1443 | 24 hours |
| 23 | Control | | None | 769 | 24 hours |
| 24 | Control | | T 99.6 F, HA, malaise, gurgling, cramps | 904+ | 40 hours |

•Did not colonize or subsequently seroconvert after vaccination
+ Two liquid stools not weight due to urgency Construction of *V. cholerae* vaccines expressing heterologous antigens The procedures described above can be applied by any artisan skilled in the art for the construction of derivatives of Peru-2, Bang-2, Bah-2, Peru-14, and related strains which are capable of expressing a wide variety of foreign or heterologous antigens, e.g., antigens that are not normally expressed in *V. cholerae*. Such derivatives, when used as live vaccines, would be expected to induce a strong immune response against both *V. cholerae* antigens and the foreign antigen that it encodes. Both systemic and local immune responses will likely be induced because vaccination with other prototype *V. cholerae* vaccines has resulted in the induction of circulating IgG and local IgA antibodies that are specific for both whole cell antigens (e.g., LPS) and as well as individual proteins such as cholera toxin B subunit (Herrington et al., 1988, J. Exp. Med. 168:1487–1492). A foreign antigen expressed by *V. cholerae* would be expected to elicit an immune response similar to that of the individual cholera proteins.

The methods useful for the introduction of heterologous antigens into *V. cholerae* are similar to those described above for the re-introduction of the ctxB gene into vaccine strains Peru-3, Peru-4, Peru-14, Peru-5, Bang-3, Bah-3 and Bah-4. Virtually any heterologous antigen can be inserted into *V. cholerae* using these methods.

The same protocol used to construct ctxB containing strains under a novel promoter can be used to construct derivatives of Peru-2, Bang-2 and Bah-2 which are capable of expression virtually any heterologous antigen or antigens normally encoded by either bacteria, viruses, or parasites. The methods described in the invention therefore teach generation of a multivalent *V. cholerae* vaccine "carrier strain" which can be manipulated to encode and express other antigens and can be administered to humans in order to immunize them against not only cholera, but other pathogens as well.

*V. cholerae*/enterotoxigenic *E. coli* vaccines

*Vibrio cholerae* vaccines which elicit antibodies against cholera toxin (CT) have been demonstrated to confer cross protection to human vaccinees against strains of heat-labile toxin (LT) producing enterotoxigenic *E. coli* (ETEC) (Svennerholm, J. Infect. Dis., 149:884–893,1984). Vaccinees were still vulnerable however to heat-stable toxin (ST) producing strains of ETEC. An attenuated strain of *Vibrio cholerae*, Peru-3, can be used as a vaccine vector harboring ETEC-derived foreign genes encoding the major subunit of colonization factor antigen CFA/IV fimbriae, and a genetic toxoid of ST. Such a vaccine vector will elicit i) anti-fimbrial antibodies, precluding binding of pathogenic ETEC strains to the human gut epithelium, and ii) anti-ST antibodies, negating the diarrheal effects of ST. The result is a single dose orally administered live attenuated *V. cholerae* vectored ETEC vaccine.

The attenuated *V. cholerae* vectored ETEC vaccine may have one or more of the following advantages: i) it can be lyophilized for long-term storage, ii) it requires no cold-chain, iii) it is orally administered, iv) it requires only a single-dose, v) it is cost effective, and vi) it protects against most ETEC strains.

A single-dose live oral vaccine directed against the enteric pathogens, *V. cholerae* and enterotoxigenic *E. coli* (ETEC) is made by genetically engineering sequences encoding antigens from *E. coli* into the *V. cholerae* vaccine strains. In the construction of such vaccine strains, it is desirable to neutralize both colonization and toxin production. This can be achieved by modifying an attenuated strain of *V. cholerae*, Peru-3 as described above.

Peru-3 strain already expresses cholera toxin B subunit which is nearly identical to the ETEC heat-labile toxin B subunit, and elicits cross protective antibodies. The strain can be modified to express fimbrial antigens of ETEC and a chimeric protein made up of the oligomerization domain of cholera toxin A subunit and a mutant form of the ETEC heat-stable toxin. In this way, the induction of immunity to both *V. cholerae* and *E. coli* can be accomplished.

The generation of the *V. cholerae*/ETEC vaccine strain is accomplished by utilizing common techniques in microbiology and molecular biology. The ability of the strain to colonize animals and induce an immune response can be analyzed in an established model of enteric infection of rabbits.

Cloning and expression of fimbrial antigens

The ability of ETEC to colonize the intestinal epithelium of humans is mediated by serologically distinct fimbriae known as colonization factor antigens (CFAs) and putative colonization factors (PCFs). The CFA/4 fimbriae is the principal colonization factor identified in approximately one quarter to one third of all ETEC clinical isolates. The gene encoding the major subunit of a prototype member of the group (CS6) has been cloned and sequenced by others.

The cloned CS6 gene carried on a high-copy number plasmid was introduced to Peru-3 via electrotransformation and maintained by culture in Luria-Bertani broth containing 50 $\mu$g/ml of ampicillin. Whole cell lysates of Peru-3 containing the CS6 sequences were analyzed for protein antigen expression by denaturing polyacrylamide gel electrophoresis and immunoblotting using anti-CS6 polyclonal rabbit serum. Immunoblots were developed using anti-rabbit IgG-alkaline phosphatase conjugate and BCIP. Expression of the CS6 gene was detected as production of a 17-kiloDalton protein. Thus CS6 antigen can be expressed in Peru-3 for the formulation of a vaccine.

In order to generate the candidate vaccine strain, however, it is desirable to have the CS6 gene stably maintained in the absence of antibiotic selection and to have it expressed from a promoter that is actively transcribed by *V. cholerae*. To that end, the polymerase chain reaction (PCR) can be used to specifically amplify the CS6 gene carried on a plasmid and to create unique restriction endonuclease sites at its termini for subsequent cloning into an ampicillin resistant, streptomycin sensitive "suicide" vector which allows integration onto the chromosome of *V. cholerae*. Specifically, PCR generated CS6 DNA flanked with a 5' PacI site and a 3' NotI site can be ligated with pJM6891 DNA which has been digested with PacI and NotI, placing the CS6 gene under the control of the cholera toxin promoter. The ligation mixture can be introduced by electrotransformation into *E. coli* strain SM10pir which provides a specific trans-acting protein, known as pi, required by pJM6891 for replication. However, when pJM6891 and its derivatives are introduced into *V. cholerae* (which lacks the pi protein), selection for resistance to 50 $\mu$g/ml of ampicillin requires that the plasmid integrate onto the chromosome. The site of integration is determined by the presence of *V. cholerae* lacZ DNA sequences flanking CS6 which are identical to sequences on the *V. cholerae* chromosome and allow homologous recombination to occur. The resulting progeny is ampicillin resistant and harbors an integrated copy of the plasmid and CS6 sequences surrounded by repeated DNA sequences of the lacZ gene.

The repeats can be resolved to remove the vector sequences (including the ampicillin resistance determinant), leaving the CS6 gene under control of the toxin promoter. This is performed by culturing the strain in the presence of 2 mg/ml of streptomycin, selecting for the streptomycin resistance allele native to Peru-3 and against the streptomycin sensitivity allele introduced by the plasmid. After growth overnight in the presence of streptomycin, the culture is plated for single colonies on LB agar containing 100 $\mu$g/ml streptomycin, and scored for sensitivity to 50 $\mu$g/ml ampicillin. Isolates that are streptomycin sensitive and ampicillin resistant will be analyzed by Southern blots of chromosomal DNA to determine if the expected integration and excision events have occurred.

These isolates can be analyzed for level of antigen production using immunoblotting techniques. Production of CS6 fimbrial antigen can be evaluated under a variety of growth conditions known to affect transcription of the cholera toxin promoter. The effect of media pH (6.5 versus 8.0), temperature (30° C. versus 37° C.), NaCl concentration (50 to 500 mM) and amino acid concentration (0 to 25 mM) on the level of CS6 expression can be determined.

The candidate vaccine strain Peru-3/CS6 can then be used in a rabbit model to demonstrate safety and immunogenicity. Since the human clinical isolates of ETEC that produce CFA antigens are typically not pathogenic to laboratory animals, another Peru-3 derivative expressing the AF/R1 fimbrial antigen of the *E. coli* strain RDEC-1 can be constructed in order to demonstrate safety and immunogenicity. This antigen mediates adherence to gut epithelium, causing a diarrheal disease in rabbits. The gene encoding AF/R1, carried on the plasmid pW1 can be amplified by PCR, cloned into pJM6891 and integrated into the chromosome in the same manner as for CS6. The level of AF/R1 expression can be evaluated by immunoblotting. While this will not produce a vaccine candidates for humans, it can serve as a model for demonstrating the expression of heterologous antigen by modified Peru-3 strains and the induction of protection from challenge by a heterologous organism.

The cloned AF/R1 gene carried on a high-copy number plasmid was also introduced to Peru-3 via electrotransformation and maintained by culture in Luria-Bertani broth containing 50 $\mu$g/ml of ampicillin. Whole cell lysates of Peru-3 containing the AF/R1 sequences were analyzed for protein antigen expression by denaturing polyacrylamide gel electrophoresis and immunoblotting using anti-AF/R1 polyclonal rabbit serum. Immunoblots were developed using anti-rabbit IgG-alkaline phosphatase conjugate and BCIP. Expression of the AF/R1 gene was detected as production of approximately 18-kiloDalton protein. Thus AF/R1 antigen can be expressed in Peru-3 for the formulation of a vaccine.

Using similar strategies, a vaccine strain expressing protective antigens of Shigella, such as lipopolysaccharide (LPS) and plasmid-derived invasive protein, can be made to protect against infectious diarrhea caused by infective species of Shigella, such as *S. sonnei.*

In *S. sonnei*, there is only one serotype of LPS and it is the primary antigenic determinant in protection against this bacteria. Introduction of a plasmid clone encoding the LPS operon into *E. coli* results in expression of LPS and is sufficient to confer upon *E. coli* the ability to be agglutinated by anti-*S. sonnei* LPS antibodies. The same plasmid introduced into the Peru-3 deletion mutant strain renders it agglutinatable. Further analysis of the operon indicated that a 12 kilobase EcoR1/BamH1 fragment of this plasmid subcloned into pBR322 still confers the agglutination phenotype. This fragment can then be introduced to the chromosome at the lacZ gene of *V. cholerae* as described above.

Construction and safety of ST-CTA2 fusions.

ETEC causes diarrhea by colonization and production of two distinct toxins. The heat-labile toxin (LT) is nearly identical in sequence, structure and biological action to cholera toxin (CT). Therefore, production of CT by Peru-3 derivatives is sufficient to induce antibodies capable of neutralizing both toxins. However, immunization with CT cannot confer protection from the ETEC heat-stable toxin (ST) which is a very small (19 amino acids) polypeptide produced by many clinical isolates, some of which do not produce LT. Thus a critical element in the candidate cholera/ ETEC vaccine is the inclusion of ST sequences in Peru-3 in order to induce antibodies to this toxin.

A number of well defined derivatives of ST have been generated that are devoid of toxin activity (SToxoids). These derivatives are typically fragments of the toxin or substitution mutations in cysteine residues that form the three disulfide bonds of the protein. An SToxoid made up of the entire mature polypeptide with cysteine to alanine mutations in residues 5 and 10 can be constructed to minimize or eliminate toxic activity. The gene encoding this SToxoid can be made entirely from complementary oligonucleotides produced with a DNA synthesizer. The synthetic gene can be flanked by unique restriction endonuclease sites for subsequent subcloning into plasmid vectors.

The size of ST (19 amino acids) renders it an inherently poor immunogen. If intact ST or even small peptide fragments are coupled chemically or genetically to other larger proteins (a carrier), ST becomes a much better immunogen and can induce neutralizing antibodies. The principal carrier used was the B subunit of LT or CT. Since foreign proteins fused to the cholera toxin A2 subunit (the domain of the enzymatic subunit which allows the A fragment to oligomerize with the B subunit pentamer) can bind to the pentamer and form holotoxinlike complexes, these chimeric complexes are i) secreted by *V. cholerae*, ii) capable of binding the ganglioside receptor, and iii) immunoreactive.

The synthetic gene encoding SToxoid can be fused, in frame, to the 5' end of the gene encoding CT A2 creating an SToxoid-A2 chimera. The gene fusion construct can be integrated onto the Peru-3 chromosome as described above. When co-expressed with CT B subunit, this protein can form holotoxin-like complexes devoid of both ST and CT biological activity and capable of binding the ganglioside receptors. Strains expressing the SToxoid-A2 chimeric protein can be analyzed by immunoblots using anti-ST antiserum to determine if the substitution mutations result in an antigenically related protein. The SToxoids can also be compared for toxicity in the infant mouse assay.

The infant mouse assay is carried out as follows. 2–3 day old mice are injected intragastrically with protein extracts derived from these vaccine strains (or purified ST as a control), sacrificed 3–4 hours after injection and examined for increased gut-to-body weight ratio. Candidate SToxoid-A2 chimeras demonstrating the lowest toxicity, can then be analyzed for immunogenicity in rabbits.

Safety, immunogenicity and efficacy of Peru-3/AF/R1.

Initial testing of the Peru-3 expressing AF/R1 can be done in rabbits. Bacteria can be administered orally at doses of $2\times10^2$, $2\times10^4$, $2\times10^6$, and $2\times10^8$ to New Zealand White rabbits. Stool samples can be collected and cultured on LB agar plates with 100 $\mu$g/ml streptomycin to enumerate colonization and shedding of bacteria. Blood can be drawn before administration of the vaccine as well as 7, 14, 21 and 28 days following administration. Sera can be prepared and analyzed for the presence of antibodies specific for AF/R1 protein via an enzyme-linked immunosorbant assay (ELISA) using purified AF/R1 bound to microtiter plates, and ability to agglutinate RDEC-1 bacteria.

Animals receiving the Peru-3/AF/R1 strain can be subsequently challenged with a pathogenic strain of RDEC-1. A challenge dose of $2\times10^6$ organisms can be administered orally to immunized and naive rabbits and stool samples observed for diarrhea (defined as loose, wet stool soiling the rectal area and loose stool in the cage bottom). Diarrhea typically occurs within 3–4 days in non-immune animals. To assay colonization, rectal swab samples are cultured on lactose MacConkey agar plates and lactose positive colonies are scored for positive reaction with anti-RDEC-1 antibodies in a slide agglutination test. Protection can be defined as both inhibition of diarrhea and bacterial colonization after day four.

Safety and immunogenicity of Peru-3/CS6 and Peru-3/ SToxoid

Initial testing of the Peru-3 strains expressing CS6 and SToxoid-A2 can be done as described above. Sera can be prepared and analyzed for the presence of antibodies specific for either CS6 or SToxoid-A2 chimeric protein via an enzyme-linked immunosorbant assay (ELISA) using purified CS6 or ganglioside bound to microtiter plates. The anti-CS6 sera can also be analyzed for the presence of antibodies capable of fixing complement and lysing CS6 producing *E. coli*. In this assay, bacteria bearing CS6 are mixed with serum and guinea pig complement, LB broth is added, and the bacteria are plated on LB agar. Bacteriocidal activity results in a decrease in the viable counts recovered. Finally, the anti-SToxoid-A2 sera can be tested for antibodies capable of neutralizing ST activity in the infant mouse toxicity assay.

Construction of attenuated *Vibrio cholera* expressing HIV-1 antigen as recombinant cholera holotoxoid An approach similar to that described above can be used to construct a *V. cholerae* vaccine strain expressing antigens of the Human Immunodeficiency Virus (HIV).

A cholera shuttle plasmid which contains a bacterial transcription unit including the promoter of the heat shock protein, htp, and the cholera CT-B gene was constructed. The transcription unit is flanked by the DNA sequences derived from the recA locus of cholera so that the CT-B gene and its promoter can be integrated into the cholera chromosome by the homologous recombination between the DNA sequence presence both in the recA locus of the cholera genome and on the plasmid. The shuttle plasmid also contains a gene encoding ampicillin resistantance and a gene encoding streptomycin sensitivity as the selection markers.

The HIV-1 envelope protein can be expressed as a part of recombinant *V. cholerae* holotoxoid secreted by the bacteria, in the form of a "sandwich" fusion protein, in which the HIV antigen is preceded by the signal sequences of the CT-A polypeptide and followed by the CT-A2 domain. The signal sequences of the CT-A and its upstream untranslated region are required for the expression and secretion of the HIV-1 antigen in the bacteria. The CT-A2 domain fused to the HIV-1 antigen is required for the fusion protein to assemble with the CT-B proteins to form a recombinant cholera holotoxoid. The plasmid described above can be modified such that a PCR fragment containing the Shine-Dalgano (SD) sequences and the signal sequences of the CT-A gene, and a unique restriction endonuclease PmeI site for inserting the HIV-1 antigen is inserted into its PacI site. The plasmid can further be modified such that a second PCR fragment containing both the CT-A2 domain and the CT-B gene replaces the CT-B gene. The orientation of the DNA insertion and the junction of the PCR fragment can be confirmed by DNA sequencing.

The HIV-1 antigen used in this study is a part of the HIV-1 envelope glycoprotein containing the principle neutralizing domain (PND). Previous studies demonstrate that a group of synthetic peptides derived from the PND can elicit neutralizing antibody in animals. A DNA fragment derived from HIV-LAI envelope gene including the PND, but without the signal sequences and the first 120 amino acids, is cloned into the PmeI site of the plasmid described above which contains both the CT-A2 domain and the CT-B gene. The in frame fusion of HIV-1 antigen and the CT-A signal peptide and CT-A2 domain can be confirmed by DNA sequencing.

To construct a genetically attenuated cholera strain that carries the HIV-1 antigen, Peru-2 is used the parental strain. The plasmid containing HIV sequences can be introduced into Peru-2 strain by mating. A recombinant strain of *V. cholera* which contains deletions of ctx and recA loci and expresses a non-toxic recombinant fusion protein of HIV-1 antigen was produced and named Peru101. Southern Blot analysis can be used to confirm that Peru101 contains the DNA for HIV-1 antigen and Western blot analysis can be used to demonstrate the expression of HIV-A2 fusion protein by the recombinant bacteria. An ELISA using both anti-CT-B and anti-HIV antibodies can test if the recombinant cholera holotoxoid is secreted by the bacteria.

Preclinical evaluation in primates of immunogenicity and protective efficacy of the oral HIV 1 vaccines using SHIV model To test the immunogenicity of *V. cholerae* recombinant Peru101 as an oral HIV-1 prophylactic vaccine, each of six adult female Rhesus monkeys (*Macaca mulatta*) can be given $2\times10^6$ CFU freshly prepared live bacteria in 30 ml bicarbonated water. Two additional animals in the same age and sex group can be given the same dose of Peru 2 as a control. The stool samples of the animals can be analyzed two days after the vaccination to detect the multiplication of *Vibrio cholera* in the intestines by determining the colony forming unit on the LB streptomycin plates. The vaginal, rectal, salivary and serum antibodies, including IgA and IgG, that are specific to HIV1 and to the CT-B can be examined biweekly post vaccination. The host animal's T cell proliferation and CTL responses that are specific to the input HIV1 antigen can also be examined. One or several boosts by oral, or by intramuscular and intravenous injection of purified HIV1 antigen may be necessary, depending upon the level of the initial immune responses of the vaccinated animals.

If Peru101 is able to stimulate the animals to generate anti-HIV antibodies or cell mediated HIV1 specific immune responses, the efficacy of Peru101 as HIV1 vaccine can be tested by challenging the animals with live SHIV-LAI stocks through vaginal infusion. The two Peru 2 animals (the monkeys who received Peru2 strain) and two of the six Peru101 animals (the monkeys who received Peru101) can be challenged by 2× VI-$AID_{50}$ dose. Two of the other Peru101 animals will receive 10× VI-$AID_{50}$ and the rest of the Peru101 monkeys will receive a maximum of 50× VI-$AID_{50}$ dose. The peripheral blood samples can be collected every two weeks post infection to determine if the animal becomes infected by detecting the viral antigen in the cultured PBMC. If the vaccine has prophylactic effect on the animals against the challenge by the SHIV carrying homologous HIV1 envelope gene, SHIV-Eli, which contains a heterologous HIV1 envelope, can be used to re-challenge the animals.

Use of the Live Vaccine Strains

The *V. cholerae* mutant strains Peru-1, Peru-2, Bang-1, Bang-2, Bah-1, Bah-2, Bengal -2, Bengal -3, Peru-14, and the additional mutants described above are useful as sources of immunological protection against cholera and other related toxigenic diseases when used as live vaccines. Other such diseases include, but are not limited to, those induced by enterotoxigenic *E. coli* and other bacteria that produce toxins which are immunologically cross-neutralizable with cholera B subunit.

When inoculated into the intestine of an experimental animal or human, mutant strains of *V. cholerae* should stimulate and induce a strong immunological response against all bacterial components that are elaborated by these strains including, but not limited to, the Ogawa and Inaba 01 LPS antigens, flagella antigens, the antigenic domains of the Tcp pili, and the outermembrane proteins. Based on published studies with other prototype cholera vaccines, both IgA and IgG classes of antibodies directed against these bacterial components will be synthesized in the inoculated animal or human and will serve to protect the animal or human against subsequent challenge with virulent strains of *V. cholerae.*

Dosage

Determination of the appropriate dosage and administration of these vaccines is performed essentially as described in Herrington et al., (1988, J. Exper. Med. 168:1487–1492). In general, such dosages are between, but are not limited to, $10^5$–$10^9$ viable bacteria per dose.

Growth of Vaccine Strains

The bacteria to be used as the vaccine can be grown in a standard *V. Cholerae* laboratory media. The cells can be harvested and then lyophilized in a formulation that preserves viability (e.g., sterile skim milk or saline containing 5 mM $CaCl_2$ and 10% weight by volume of glycerol).

Administration

Administration of the vaccine involves combining the contents of two envelopes or vials, one containing the lyophilized vaccine strain or combination of strains, the other containing water and sufficient sodium bicarbonate or alternate buffer as to neutralize stomach acid (approximately 2 grams). The vaccine can then be swallowed by the vaccinee. Alternatively, the lyophilized vaccine can be incorporated into tablets which can be coated with an acid resistant "enteric coating". Such a form of vaccine can be administered to the vaccinee in one or more (up to three) doses spaced from a few days to several weeks apart. When used as a "booster" vaccine, the vaccine can also be administered to previously vaccinated individuals in one or more doses (up to three) spaced from a few days to several weeks apart. When two or more strains are being administered they may be provided together, or in individual doses 7–28 days apart.

Improved Killed Oral Cholera Vaccines

Preparations of improved killed oral cholera vaccines can be made from the strains described above. The experimental cholera vaccine that is currently available is comprised of approximately $10^{11}$ formalin and heat killed *V. cholerae* cells mixed with purified cholera toxin B subunit (Black et al., Infect. Immun. 55:1116, 1987). The four strains that are used in the preparation of the bacterial component of this vaccine produce active cholera toxin which must be completely inactivated before administration to the vaccinee. The new strains described above provide a vaccine that is vastly improved compared with the vaccine of Black et al. (Supra) for each of the reasons given below.

(1) Because the strains derived from, and including Peru-2, Bang-2 and Bah-2, produce only the nontoxic B subunit of the cholera toxin and not the toxic A subunit, cultures of these strains require only mild inactivation prior to administration to a vaccinee, thus avoiding the more severe denaturing treatments such as formalin or heat. The advantages of the milder treatment are that the antigens will retain a greater degree of their native configuration and as a result they will be more immunogenic. Mild methods of inactivation that avoid chemically inactivating the bacterial proteins include microwaving the organisms, treatment with another radiation source or a mild organic solvent or detergent, or the cells may be lysed by mechanical methods such as sonication or use of a French Press.

(2) In the strains Peru-3, Bang-3 and Bah-3, the ctxB gene has been placed under the control of the htp promoter. As a result, these strains synthesize large quantities of the cholera toxin B subunit (greater than 10 μg/ml of culture) in standard laboratory medium such as LB. This facilitates purification of large amounts of the cholera B subunit and thus these strains provide a significant advantage over other strains which only produce the B subunit in small quantities under stringent growth conditions.

(3) In the preparation of existing killed cholera vaccines, a separate bacterial strain is used to produce the B toxin subunit from the strain used as the whole cell antigen. During preparation of the B subunit it is therefore necessary to purify the B subunit away from the toxic A subunit using biochemical methods. Such purification incurs the risk that small amounts of the A subunit may contaminate the preparation of the B subunit. Using the strains described above, it is possible to generate a whole cell antigen preparation from the same culture used to obtain the B subunit preparation. In the first instance, purification of the B subunit is now unnecessary because the strain does not produce the A subunit, thus reducing the amount of time and considerable expense involved in production of the vaccine. Secondly, there is no risk of having any contaminating A subunit in the preparations since the bacteria simply do not encode the gene for this subunit and therefore cannot produce it. The whole cell preparation can therefore be used as a vaccine with minimal risk to the vaccinee.

(4) Some bacterial strains of the invention are derivatives of *V. cholerae* of the El Tor biotype and more particularly, in the case of Peru-2, Peru-3 and Peru-4, they are derivatives of an isolate (C6709-Sm) which is in fact the causative agent of the current epidemic in Latin America. If there are antigens that are unique to this particular parental strain, the vaccine derivatives described above may provide generally better protection against El Tor disease in Latin America and possibly other areas in the world.

Preparation of Improved Oral Killed Cholera Vaccines

An improved oral killed cholera vaccine can be prepared as follows. A minimum of two strains, preferably, selected from the Ogawa serotype (e.g., Bah-3), to the Inaba serotype (e.g., Peru-3, Peru-14, or Bang-3), and the Bengal serotype (e.g., Bengal-2 or Bengal-3) can be grown in separate cultures. One of ordinary skill in the art will know how to adjust the conditions, media, etc. to maximize cell growth at 37° C. For example, cultures grown under a high level of aeration in a medium such as CYE (Mekalanos et al., 1977, Infect. Immun. 16:789) or minimal medium containing glucose, i.e., AGM4 (van de Walle et al., 1990, Appl. Microbiol. Biotechnol. 33:389) can be used. When growth of the bacteria has reached saturation, whole cells can be recovered from the medium by centrifugation, while proteins (including the B subunit) contained within the supernatant fraction can be obtained by ultracentrifugation or by precipitation. The cells can be inactivated using the methods of Black et al. (Infect. Immun. 55:1116, 1987) or by milder methods (e.g., microwaving, irradiation using alpha, beta or gamma rays), treatment with organic solvents such as ethanol or acetone, or they may be lysed by treatment with either a detergent or by mechanical methods, such as sonication or by using a French Press. The inactivated cells can then be combined with filtered, concentrated supernatant containing bacterial proteins (including subunit B) and the mixture can be suspended in a pharmaceutically acceptable solution appropriate for oral administration (e.g., sterile saline or 2% sodium bicarbonate).

Administration

The vaccine can be administered to the vaccinee as an oral saline solution which is swallowed by the vaccinee several minutes after the vaccinee has ingested 2 grams of sodium bicarbonate. Alternatively, the preparation can be lyophilized and compressed into tablets which are then coated with an acid-resistant "enteric coating" prior to administration to the vaccinee. The tablets can also be microencapsulated with polymers in order to facilitate uptake of the preparation by the intestinal mucosal tissue.

Dosage

A single dose of vaccine should contain approximately $10^{11}$ cells and approximately 100–5000 μg of cholera B subunit. It is expected that the vaccinee will require approximately two or more separate doses of vaccine administered approximately two or more weeks apart.

Deposit

Under the terms of the Budapest Treaty on the International Recognition of the Deposit of Microorganisms for the Purpose of Patent Procedure, deposit of *V. cholerae* strains C6709-Sm, P27459-Sm, E7946-Sm, Bengal-2, Bengal-3, MO10, Peru-5 and Peru-14 have been made with the American Type Culture Collection (ATCC) of 12301 Parklawn Drive Rockville, Md., 20852 U.S.A., where the deposits were given ATCC Accession Numbers ATCC 55331 (C6709-Sm); ATCC 55333 (P27459-Sm); ATCC 55332 (E7946-Sm); ATCC 55436 (0139, Bengal-2; ATCC 55437 (0139, Bengal-3); ATCC 55438 (0139, MO10) ATCC 55868 (Peru-5 ); and ATCC 55446 (Peru-14).

The following *V cholerae* strains were also deposited and given ATCC numbers: Bah-2 (ATCC 55859); Bah-3 (ATCC 55860); Bang-2(ATCC 55862); Bang-3 (ATCC 55863); Peru-2 (ATCC 55865); Peru-3 (ATCC 55866); and Peru-4 (ATCC 55867).

Applicant's assignee, President and Fellows of Harvard College, represents that the ATCC is a depository affording permanence of the deposit and ready accessibility thereto by the public if a patent is granted. All restrictions on the availability to the public of the material so deposited will be irrevocably removed upon granting of a patent. The material will be available during the pendency of the patent application to one determined by the Commissioner to be entitled thereto under 37 C.F.R. 1.14 and 35 U.S.C. § 122. The deposited material will be maintained with all the care necessary to keep it viable and uncontaminated for a period of at least five years after the most recent request for the furnishing of a sample of the deposited material, and in any case, for a period of at least thirty (30) years after the date of deposit or for the enforceable life of the patent, whichever period is longer. Applicant's assignee acknowledges its duty to replace the deposit should the depository be unable to furnish a sample when requested due to the condition of the deposit.

SEQUENCE LISTING

<160>6

<210>1
<211>17
<212>DNA
<213>Vibrio cholerae

<400>1
cctagtgcgc attatgt 17

<210>2
<211>52
<212>DNA
<213>Vibrio cholerae

<400>2
taaacctaga gacaaaatgt tcctagtgcg cattatgtat gttatgttaa at 52

<210>3
<211>48
<212>DNA
<213>Vibrio cholerae

<400>3
taaacctaga gacaaaatgt tcctagtgcg cattatgtgg cgcggcat 48

<210>4
<211>50
<212>DNA
<213>Vibrio cholerae

<400>4
aaaccctaga ttccgccgcc ttagtgcgca ttatgtatgt tatgttaaat 50

<210>5
<211>32
<212>DNA
<213>Vibrio cholerae

<400>5
gggctaaagt taaaagacaa atattttcag gc 32

<210>6
<211>26

-continued

< 2 1 2 >DNA

< 2 1 3 >Vibrio cholerae

< 4 0 0 >6 g g g t a g a a g t  g a a a c g g g g t  t t a c c g  2 6

What is claimed is:

1. A nontoxinogenic genetically stable mutant strain of *Vibrio cholerae*, said mutant strain comprising a genetically engineered deletion of DNA encoding a CtxA subunit such that said mutant strain lacks a reactogenic subunit A of cholera toxin, said mutant strain further comprising deletions at attRS1 sequences, said strain further having at least 1000-fold lower attRS1 mediated recombination relative to a parent strain lacking deletions of attRS1, and said mutant strain further comprising DNA encoding an expressed heterologous antigen.

2. The mutant *Vibrio cholerae* strain of claim 1, wherein said mutant strain is derived from a strain belonging to the El Tor serogroup.

3. The mutant *Vibrio cholerae* strain of claim 1, wherein said mutant strain is derived from a strain belonging to the Inaba or Ogawa serotype.

4. The *Vibrio cholerae* strain of claim 3, wherein said strain is derived from Peru-14 (ATCC 55446).

5. The mutant *Vibrio cholerae* strain of claim 3, wherein said strain is derived from a strain which is Peru-2 (ATCC 55865), Bang-2 (ATCC 55862) or Bah-2 (ATCC 55860).

6. The mutant *Vibrio cholerae* strain of claim 1, wherein said mutant strain is derived from a strain belonging to the non-01 serogroup.

7. The mutant *Vibrio cholerae* strain of claim 6, wherein said mutant strain is derived from a strain belonging to the Bengal serogroup.

8. The mutant *Vibrio cholerae* strain of claim 1, wherein said mutant strain further lacks a functional recA gene.

9. The mutant *Vibrio cholerae* strain of claim 1, wherein said mutant strain lacks CTX core sequence.

10. The *Vibrio cholerae* strain of claim 1, wherein the recA gene of said strain is inactivated.

11. The mutant *Vibrio cholerae* strain of claim 1, wherein said strain further encodes a B subunit of cholera toxin.

12. The mutant *Vibrio cholerae* strain of claim 1, wherein said heterologous antigen is a Shiga-like toxin, a Shigella lipopolysaccharide antigen, or an *Escherichia coli* fimbrial antigen.

13. The *Vibrio cholerae* strain of claim 1, wherein the DNA encoding said heterologous antigen is inserted into the lacZ gene of said mutant *Vibrio cholerae.*

14. The mutant *Vibrio cholerae* strain of claim 1, wherein said mutant strain is derived from a strain which is Peru-3 (ATCC 55866), Peru-4 (ATCC 55867), Bang-3 (ATCC 55863), Bah-3 (ATCC 55860), or a Bah serogroup strain.

15. The mutant strain of claim 1, wherein said mutant strain has a deletion of all attRS1 sequences.

16. The mutant strain of claim 1, wherein said heterologous antigen is Shiga-like toxin.

17. The mutant strain of claim 1, wherein said heterologous antigen is Shigella lipopolysaccharide antigen.

18. The mutant strain of claim 1, wherein said hetrologous antigen is *Escherichia coli* fimbrial antigen.

19. The mutant strain of claim 1, wherein said heterologous antigen is a CFA antigen of an enterotoxigenic *Escherichia coli* strain.

20. The mutant strain of claim 1, wherein said heterologous antigen is anthrax toxin.

21. The mutant strain of claim 1, wherein said heterologous antigen is pertussis toxin.

22. The mutant strain of claim 1, wherein said heterologous antigen is tetanus toxin.

23. The mutant strain of claim 1, wherein said heterologous antigen is from herpes virus.

24. The mutant strain of claim 1, wherein said heterologous antigen is from rubella virus.

25. The mutant strain of claim 1, wherein sad heterologous antigen is from influenza virus.

26. The mutant strain of claim 1, where said heterologous antigen is from mumps virus.

27. The mutant strain of claim 1, wherein said heterologous antigen is from measles virus.

28. The mutant strain of claim 1, wherein said heterologous antigen is from poliomyelitis virus.

29. The mutant strain of claim 1, wherein said heterologous antigen is from a eukaryotic parasite causing malaria.

30. The mutant strain of claim 1, wherein said heterologous antigen is from pneumocystis pneumonia.

31. The mutant strain of claim 1, wherein said heterologous antigen is from toxoplasmosis.

32. A method of making a killed *Vibrio cholerae* strain vaccine, said method comprising the steps of providing at least a *Vibrio cholerae* mutant strain of claim 1, which strain has been killed;

adding to said killed strain a cholera toxin B, wherein said toxin B subunit is obtained from the medium in which said mutant strain was propagated.

33. A vaccine comprising at least two different strains of mutant *Vibrio cholerae* strain according to claim 27, one of said strains being derived from Peru and the other being derived from Bengal.

34. A killed oral cholera vaccine, said vaccine comprising at least a first and a second *Vibrio cholerae* strain suspended in a physiologically acceptable carrier, wherein each strain lacks DNA encoding a functional ctxA subunit, wherein at least two of said strains are different serotypes, said *Vibrio cholerae* being non-viable, said vaccine further comprising cholera toxin B subunit which is overproduced by at least one of said serotypes of said *Vibrio cholerae* strain and wherein at least one of said strains is a strain of claim 1.

35. The vaccine of claim 34, wherein one of said serotypes is an Ogawa serotype and another of said serotypes is an Inaba serotype.

36. The vaccine of claim 35, wherein said vaccine comprises Bah-3 (ATCC 55860) and either Peru-3 (ATCC 55866) or Bang-3 (ATCC 55863); or both Peru-3 (ATCC 55866) and Bang-3 (ATCC 55863).

37. A method of making a killed *V. cholerae* vaccine, said method comprising the steps of providing at least the first and second *V. cholerae* strains of claim 34, which strains have been killed;

adding to said killed strains cholera toxin B subunit produced by at least one of said strains, wherein said toxin B subunit is obtained from the medium in which one of said strains was propagated; and suspending said killed strains and said toxin B subunit in a physiologically acceptable carrier.

38. A method of making a genetically stable mutant strain of *Vibrio cholerae* comprising a deletion of DNA encoding the ctxA subunit such that said mutant strain lacks a reactogenic subunit A of cholera toxin, and said mutant strain further comprising a deletion of attRS1 sequences, and having at least 1000-fold lower attRS1 mediated recombination than a parent strain having at least two copies of attRS1, and said mutant strain further comprising a heterologous antigen, said method comprising:

introducing into a wild type *Vibrio cholerae* a plasmid comprising a fragment of *Vibrio cholerae* DNA which is mutated in its ctxA and attRS1 sequences, said DNA being capable of recombining with wild type *Vibrio cholerae* DNA inside said wild type *Vibrio cholerae* resulting in the generation of said mutant strain, and said method further comprising introducing into the wild type *Vibrio cholerae* a DNA encoding a heterologous antigen.

39. The method of claim 38, wherein said mutant strain is derived from a strain which is Peru-2 (ATCC 55865), Bang-2 (ATCC 55862), or Bah-2 (ATCC 55860).

40. The method of claim 38, wherein said mutant strain lacks CTX core sequences.

41. The method of claim 38, wherein the recA gene of said mutant strain is inactivated.

42. The method of claim 38, wherein said method further comprises introducing into the lacZ gene of said mutant strain a fragment of DNA encoding an antigen.

43. The method of claim 42, wherein said mutant strain is derived from a strain which is Peru-5 (ATCC 55868).

44. The method of claim 38, wherein said mutant strain has a deletion of all attRS1 sequences.

* * * * *